(12) United States Patent  
Rodriguez et al.

(10) Patent No.: US 9,961,904 B2  
(45) Date of Patent: May 8, 2018

(54) COMPOSITIONS AND METHODS RELATED TO ISOLATED ENDOPHYTES

(71) Applicant: Adaptive Symbiotic Technologies LLC, Seattle, WA (US)

(72) Inventors: Russell John Rodriguez, Seattle, WA (US); Regina Soon Redman, Seattle, WA (US)

(73) Assignee: Adaptive Symbiotic Technologies LLC, Seattle, WA (US)

( * ) Notice: Subject to any disclaimer, the term of this patent is extended or adjusted under 35 U.S.C. 154(b) by 498 days.

(21) Appl. No.: 14/340,597

(22) Filed: Jul. 25, 2014

(65) Prior Publication Data

US 2015/0033420 A1    Jan. 29, 2015

Related U.S. Application Data

(60) Provisional application No. 61/858,819, filed on Jul. 26, 2013.

(51) Int. Cl.
*A01N 63/04* (2006.01)
*C12N 1/14* (2006.01)
*C12R 1/885* (2006.01)

(52) U.S. Cl.
CPC .............. *A01N 63/04* (2013.01); *C12N 1/14* (2013.01); *C12R 1/885* (2013.01)

(58) Field of Classification Search
None
See application file for complete search history.

(56) References Cited

U.S. PATENT DOCUMENTS

| 7,906,313 B2 | 3/2011 | Henson et al. |
| 8,598,083 B2 | 12/2013 | Kaminskyj et al. |
| 2010/0227357 A1 | 9/2010 | Redman et al. |

FOREIGN PATENT DOCUMENTS

| WO | WO 2007/110686 A2 | 10/2007 |
| WO | WO 2011/032281 A1 | 3/2011 |

OTHER PUBLICATIONS

Kleifeld et al 1992, Plant and Soil 144: 267-272.*
Altomare et al 1999, Applied and Environmental Microbiology 65(7): 2926-2933.*
Fahey et al 1991, Chapter 20 in Microbial Ecology of Leaves, Springer-Verlag New York Inc., pp. 401-411.*
[No Author Listed], AE460: Interpretation of Soil Moisture Content to Determine Soil Field Capacity and Avoid Over-Irrigating Sandy Soils Using Soil Moisture Sensors. University of Florida IFAS Extension. Figure 1. 2012.
Berg, Plant-microbe interactions promoting plant growth and health: perspectives for controlled use of microorganisms in agri-culture. Appl Microbiol Biotechnol. Aug. 2009;84(1):11-8. doi: 10.1007/s00253-009-2092-7. Epub Jul. 1, 2009.
Bowden et al., Seed Treatment. Pesticide Application Training. Category 4. 1998.
Clay et al., Fungal endophyte symbiosis and plant diversity in successional fields. Science. Sep. 10, 1999;285(5434):1742-5.
Harman et al., *Trichoderma* species—opportunistic, avirulent plant symbionts. Nat Rev Microbiol. Jan. 2004;2(1):43-56.
Naseby et al., Effect of biocontrol strains of Trichoderma on plant growth, Pythium ultimum populations, soil microbial communities and soil enzyme activities. J Appl Microbiol. Jan. 2000;88(1):161-9.
O'Donnell et al., Gene genealogies reveal global phylogeographic structure and reproductive isolation among lineages of *Fusarium graminearum*, the fungus causing wheat scab. Proc Natl Acad Sci U S A. Jul. 5, 2000;97(14):7905-10.
Reardon, Superplants may beat the heat. New Scientist. Jul. 28, 2012;215(2875):8-9.
Redman et al. Field performance of cucurbit and tomato plants infected with a nonpathogenic mutant of Colletotrichum magna (teleomorph: Glomerella magna; Jenkins and Winstead). Symbiosis. 2002a;32:55-70.
Redman et al., Biochemical analysis of plant protection afforded by a nonpathogenic endophytic mutant of Colletotrichum magna. Plant Physiol. Feb. 1999;119(2):795-804.
Redman et al., Fungal symbiosis from mutualism to parasitism: who controls the outcome, host or invader? New Phytologist. 2001;151:705-716.
Redman et al., Increased fitness of rice plants to abiotic stress via habitat adapted symbiosis: a strategy for mitigating impacts of climate change. PLoS One. 2011;6(7):e14823. doi: 10.1371/journal.pone.0014823. Epub Jul. 5, 2011.
Redman et al., Thermotolerance generated by plant/fungal symbio-sis. Science. Nov. 22, 2002; 298 (5598):1581.
Rodriguez et al., A family of conserved repetitive DNA elements from the fungal plant pathogen Glomerella cingulata (*Colletotrichum lindemuthianum*). Experimental Mycology. 1991;15:232-242.
Rodriguez et al., More than 400 million years of evolution and some plants still can't make it on their own: plant stress tolerance via fungal symbiosis. J Exp Bot. 2008;59(5):1109-14. doi: 10.1093/jxb/erm342. Epub Feb. 10, 2008
Rodriguez et al., Stress tolerance in plants via habitat-adapted symbiosis. ISME J. Apr. 2008;2(4):404-16. doi: 10.1038/ismej.2007.106. Epub Feb. 7, 2008.
Rodriguez et al., Symbiotic regulation of plant growth, development and reproduction. Commun Integr Biol. 2009;2(2):141-3.
Rodriguez et al., The role of fungal symbioses in the adaptation of plants to high stress environments. Mitigation Adaptation Strat Global Change. Jul. 2004;9(3):261-272.
Rodriguez, Polyphosphate present in DNA preparations from fila-mentous fungal species of *Colletotrichum* inhibits restriction endonucleases and other enzymes. Anal Biochem. Mar. 1993;209(2):291-7.
Tucker, Essential Plant Nutrients: Their presence in North Carolina soils and role in plant nutrition. Oct. 1999. 1-9.
White et al., Amplification and direct sequencing of fungal ribo-somal RNA genes for phylogenetics. In:Innis et al. (Eds.). PCR Protocols: A guide to methods and applications. Academic Press, INC: San Diego. 1990;315-322.

(Continued)

*Primary Examiner* — David H Kruse
(74) *Attorney, Agent, or Firm* — Wolf, Greenfield & Sacks, P.C.

(57) ABSTRACT

Described herein are compositions and methods related to isolated *Trichoderma harzianum* and strains thereof.

11 Claims, 31 Drawing Sheets

(56) References Cited

OTHER PUBLICATIONS

Bacon et al., Symptomless grass endophytes: products of coevolutionary symbioses and their role in the ecological adaptations of grasses. In: Redlin et al., (Eds.) Endophytic Fungi in Grasses and Woody Plants. St. Paul: APS Press. Chapter 8. 1996. pp. 155-178.

Petrini, Ecological and physiological aspects of host-specificity in endophytic fungi. In: Redlin et al., (Eds.) Endophytic Fungi in Grasses and Woody Plants. St. Paul: APS Press. Chapter 4. 1996. pp. 87-100.

Read, Mycorrhiza-state of the art. In: Varma et al. (Eds.) Mycorrhiza: Structure, Function, Molecular Biology and Biotechnology. Berlin, Springer-Verlag. 1999. pp. 3-34.

Rodriguez et al., Fungal life-styles and ecosystem dynamics: biological aspects of plant pathogens, plant endophytes and saprophytes. Adv. Bot. Res. 1997;24:169-193.

Rodriguez et al., Viruses, fungi and plants: cross-kingdom communication and mutualism. Biocomm Fungi. May 2012; pp. 219-227.

* cited by examiner

Field evaluation under drought stress

Shoot and Root Biomass of Corn

Root Development in Corn

NS S

Low Nutrient Stress

Root (g)

Shoot (g)

Yields (g)

Drought Stress

Root (g)

Shoot (g)

Yields (g)

Salt Stress

Salt Stress

Temperature Stress

Temperature Stress

Temperature Stress
Seed Germination – heat

Temperature Stress
Seed germination -heat

Temperature Stress
Seed Germination – cold

Temperature Stress
Seed Germination – cold

39A

39B

39C

COMPOSITIONS AND METHODS RELATED TO ISOLATED ENDOPHYTES

RELATED APPLICATION

This application is claims the benefit under 35 U.S.C. § 119(e) of U.S. provisional application Ser. No. 61/858,819, filed Jul. 26, 2013, the disclosure of which is incorporated by reference herein in its entirety.

FIELD OF THE INVENTION

The disclosure relates to isolated endophytes and uses thereof, such as for the inoculation of plants to promote stress tolerance and/or increase growth or germination.

BACKGROUND OF THE INVENTION

Symbiosis, defined as the living together of two or more organisms in close or intimate association, is often a mutually beneficial interaction between two organisms. Most plants are symbiotic with fungi (Petrini, 1986) and these fungi play important roles in the structure, function, and health and adaptation of plant communities (Bacon and Hill, 1996; Clay and Holah, 1999; Petrini, 1986; Read, 1999; Rodriguez and Redman, 1997).

It has been demonstrated that a symbiotic relationships with fungi can enhance the growth of host plants under stressful conditions. For example, specific strains of endophytic fungi confer tolerance to host plants against extreme environmental conditions including temperature, drought, and salinity (Redman et al., 2002b; Rodriguez et al., 2004; Rodriguez and Redman, 2008; Rodriguez et al., 2009; Redman et al., 2011; Rodriguez et al., 2012). Endophytes are a class of fungal symbionts that reside within host plant roots, stems and/or leaves. In addition to promoting stress tolerance, endophytes also increase nutrient acquisition and growth rates (biomass and yields) of host plants, and improve water use efficiency (Rodriguez et al., 2008; Rodriguez et al., 2009).

Abiotic stresses (such as drought, temperature, salinity, pH and nutrient) alter the physiology of plants resulting in decreased fitness, health, development and yields. Propagating plants under marginal growth conditions (typically due to abiotic stresses) would allow for an increase in agriculture production and mitigation of climate induced habitat changes for both crop and native plants. Moreover, creating new vegetation is important for soil and water remediation of polluted sites created by modern industry and other human activities.

Previous published studies (Redman et al., 2002b & 2011; Rodriguez et al., 2008 & 2012) have demonstrated that a special class of fungal symbionts (class 2) can confer biotic and abiotic stress benefits to plants simply by colonizing them with the fungal endophyte.

SUMMARY OF THE INVENTION

As described herein, it has been discovered that fungal endophytes such as *Trichoderma harzianum*, e.g., strain ThLm1, conferred superior abiotic/biotic stress tolerance and increased yields of both agricultural and native plants compared to previously identified fungal endophytes. Accordingly, aspects of the disclosure relate to compositions and methods related to isolated fungal endophytes, such as the species *T. harzianum*, including strain ThLm1.

According to one aspect of the invention, an isolated *Trichoderma harzianum* strain ThLm1 fungus is provided, deposited at the U.S. Department of Agriculture Culture Collection under Patent Deposit Designation number NRRL 50846 (date of deposit Jul. 26, 2013), or a progeny or spore thereof. Compositions comprising the *Trichoderma harzianum* strain ThLm1 fungus and/or a progeny and/or a spore thereof also are provided. The compositions include, for example, liquid compositions and powder compositions.

According to another aspect of the invention, methods for promoting stress tolerance and/or enhancing plant growth or seed germination are provided. The methods include inoculating a plant or a plant seed with the isolated *Trichoderma harzianum* strain ThLm1 fungus, or a spore or progeny thereof; or a composition thereof. In some embodiments, the stress tolerance is drought tolerance, salt tolerance, reduced nutrient tolerance, fungal tolerance, and/or temperature tolerance. In some embodiments, the enhanced plant growth or seed germination comprises an increase in size, extent of root development, germination rate of seeds, chlorophyll content/level, photosynthetic efficiency, yield or mass.

Inoculating the plant can, in some embodiments, include colonizing a root and/or stem of the plant with a *Trichoderma harzianum* strain ThLm1 fungus or a spore or progeny thereof.

In some embodiments, the method further comprises growing the plant or plant seed, which may be in soil characterized by high salinity, low moisture, and/or low nutrient content. In some embodiments, the high salinity is greater than 35 mM amount of a salt. In some embodiments, the low moisture content is between 0-0.18 in$^3$ water/in$^3$ soil. In some embodiments, the low nutrient content is fewer than 80 lbs/acre of nutrient, wherein the nutrient comprises 20% each of nitrogen, phosphorus, and potassium, and associated micronutrients.

In some embodiments, the plant or plant seed is grown in water characterized by high salinity and/or low nutrient content.

In some embodiments, the plant or plant seed is grown or germinated at an average temperature at or above 35 degrees Celsius or at or below 15 degrees Celsius.

In some embodiments, the plant or plant seed is a crop plant or crop plant seed, such as watermelon, tomato, corn, wheat, soybean, cucurbits, peppers, leafy greens, barley, cotton, beans, peas, tubers, berries, woody plants or rice, or a seed thereof. In other embodiments, the plant or plant seed is an ornamental, such as Rosaceae, Liliaceae, Azalea, Rhododendron, Poaceae or Chrysanthemum.

According to another aspect of the invention, plants or plant seeds are provided that are inoculated with the isolated *Trichoderma harzianum* strain ThLm1 fungus, or a spore or progeny thereof; or composition thereof.

In some embodiments, the plant or plant seed is a crop plant or crop plant seed, such as watermelon, tomato, corn, wheat, soybean, cucurbits, peppers, leafy greens, barley, cotton, beans, peas, tubers, berries, woody plants or rice, or a seed thereof. In other embodiments, the plant or plant seed is an ornamental, such as Rosaceae, Liliaceae, Azalea, Rhododendron, Poaceae or Chrysanthemum.

According to another aspect of the invention, methods for increasing stress tolerance are provided. The methods include inoculating a plant or a plant seed with an isolated *Trichoderma harzianum* fungus or a spore thereof; or a composition comprising the isolated *Trichoderma harzianum* fungus or a spore thereof, thereby increasing stress tolerance of the inoculated plant.

In some embodiments, the stress is drought, elevated salt, reduced nutrients and/or temperature stress. In some embodiments, the stress is not the presence of polycyclic aromatic hydrocarbons, napthenic acids, or high pH.

In some embodiments, inoculating the plant comprises colonizing a root, stem and/or leaf of the plant with a *Trichoderma harzianum* strain fungus or a spore or progeny thereof.

In some embodiments, the method further comprises growing the plant or plant seed, which may be in soil characterized by high salinity, low moisture, and/or low nutrient content. In some embodiments, the high salinity is greater than 35 mM amount of a salt. In some embodiments, the low moisture content is between 0-0.18 in$^3$ water/in$^3$ soil. In some embodiments, the low nutrient content is fewer than 80 lbs/acre of nutrient, wherein the nutrient comprises 20% each of nitrogen, phosphorus, and potassium, and associated micronutrients.

In some embodiments, the plant or plant seed is grown in water characterized by high salinity and/or low nutrient content.

In some embodiments, the plant or plant seed is grown or germinated at an average temperature at or above 35 degrees Celsius or at or below 15 degrees Celsius.

In some embodiments, the plant or plant seed is a crop plant or crop plant seed, such as watermelon, tomato, corn, wheat, soybean, cucurbits, peppers, leafy greens, barley, cotton, beans, peas, tubers, berries, woody plants or rice, or a seed thereof. In other embodiments, the plant or plant seed is an ornamental, such as Rosaceae, Liliaceae, Azalea, Rhododendron, Poaceae or Chrysanthemum.

In some embodiments, the *Trichoderma harzianum* strain fungus is not strain TSTh20-1 or strain T-22.

According to another aspect of the invention, methods for increasing germination of seeds are provided. The methods include inoculating a plant seed with an isolated *Trichoderma harzianum* fungus or a spore thereof; or a composition comprising the isolated *Trichoderma harzianum* fungus or a spore thereof, thereby increasing germination of the inoculated seeds.

In some embodiments, the plant seed is previously, concurrently and/or subsequently treated with a fungicide and/or insecticide.

In some embodiments, the plant or plant seed is a crop plant or crop plant seed, such as watermelon, tomato, corn, wheat, soybean, cucurbits, peppers, leafy greens, barley, cotton, beans, peas, tubers, berries, woody plants or rice, or a seed thereof. In other embodiments, the plant or plant seed is an ornamental, such as Rosaceae, Liliaceae, Azalea, Rhododendron, Poaceae or Chrysanthemum.

In some embodiments, the *Trichoderma harzianum* strain fungus is not strain TSTh20-1 or strain T-22.

According to another aspect of the invention, methods for reducing establishment of fungi other than *Trichoderma harzianum* in a plant are provided. The methods include inoculating a plant seed or seedling with an isolated *Trichoderma harzianum* fungus or a spore thereof; or a composition comprising the isolated *Trichoderma harzianum* fungus or a spore thereof, thereby reducing establishment of fungi other than *Trichoderma harzianum* in a plant growing from the inoculated seed or seedling.

In some embodiments, the plant or plant seed is a crop plant or crop plant seed, such as watermelon, tomato, corn, wheat, soybean, cucurbits, peppers, leafy greens, barley, cotton, beans, peas, tubers, berries, woody plants or rice, or a seed thereof. In other embodiments, the plant or plant seed is an ornamental, such as Rosaceae, Liliaceae, Azalea, Rhododendron, Poaceae or Chrysanthemum.

In some embodiments, the *Trichoderma harzianum* strain fungus is not strain TSTh20-1 or strain T-22.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 11 is a representative photograph of Nonsymbiotic (NS, left) and Symbiotic (S, right) roots from plants in FIG. 10.

DETAILED DESCRIPTION OF THE INVENTION

Figure 1:
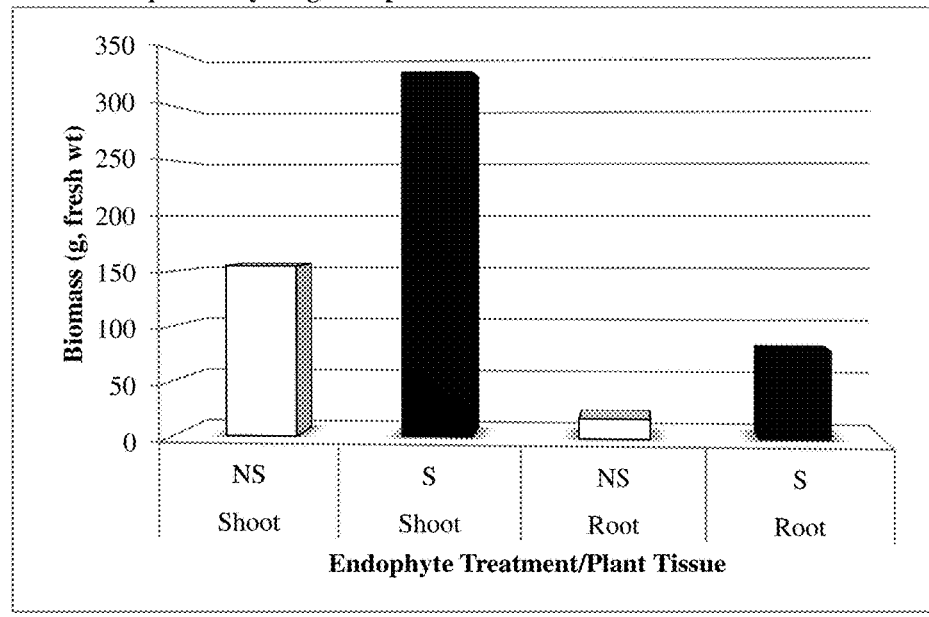
FIG. 1 is a bar graph showing the biomass response of young corn plants to ThLm1. Nonsymbiotic (NS—bars on left of each pair) and Symbiotic with ThLm1 (S—bars on right of each pair) corn plants (N=24) were grown for one month in a greenhouse without stress. Values on the Y-axes are wet weights in grams (g) with average weights shown.

In this century the foreseeable limitations on agricultural productivity include abiotic stresses such as drought, temperature extremes and salinity. Currently, there are no stress tolerant crop plants or commercial products capable of generating stress tolerant crops. Abiotic stress tolerant crops have not been generated by breeding, mutational selection or genetically modified (GM) approaches and remain a "holy grail" of agriculture.

Corn, soybean, wheat and rice are grown in great quantities around the world and are considered to be among the most important crops for sustaining the human population. However, growers are faced with many challenges in maintaining the high crop yields required for agricultural sustainability. In recent years, global climate changes have contributed to an increased frequency of severe droughts in many agricultural settings. It is possible to mitigate the impacts of drought through irrigation, however, this is a costly fix and water quality/availability is also decreasing.

There are several microbial products available that enhance growth, alter the nutrient status of plants or protect plants against microbial or insect pathogens (Table 1; Berg, 2009).

TABLE 1

Microbial products for use in agriculture

| Microbial Genus/Group | Description | Agriculture use category |
|---|---|---|
| Ampelomyces | Fungal | Disease control |
| Azospirillum | Bacterial | Growth enhancement |
| Bacillus | Bacterial | Disease control & Growth enhancement |
| Beauveria | Fungal | Insect control |
| Bradyrhizobium | Bacterial | Nutrient supplementation |
| Candida | Fungal | Post harvest disease control |
| Colletotrichum | Fungal | Weed control |
| Coniothyrium | Fungal | Disease control |
| Delftia | Bacterial | Growth enhancement |
| Erwinia | Bacterial | Disease control |
| Metarhizium | Fungal | Insect control |
| Mycorrhizae | Fungal | Nutrient acquisition |
| Paecilomyces | Fungal | Disease control |
| Coniothyrium | Fungal | Disease control |
| Phytophthora | Fungal | Weed control |
| Pichia | Fungal | Post harvest disease control |
| Pseudomonas | Bacterial | Disease control, Growth enhancement, Frost protection |
| Rhizobacteria | Bacterial | Disease control |
| Rhizobium | Bacterial | Nitrogen supplementation |
| Serratia | Bacterial | Disease control |
| Streptomyces | Bacterial | Disease control, Growth enhancement |
| Trichoderma | Fungal | Disease control |

*Trichoderma harzianum* (*T. harzianum*) is a fungal species that encompasses a wide variety of physiologically specialized strains, some of which are used as biopesticides against soil-borne plant pathogens or for the industrial production of enzymes (Naseby et al., 2000). *T. harzianum* has been shown to induce metabolic changes in plants that increase their resistance to a wide variety of plant-pathogenic microorganisms and viruses (Harman et al., 2004). It has previously been shown that *T. harzianum* strain T-22, can increase the growth of plant and root development under some conditions. T-22 can also solubilize plant nutrients for plant uptake that would otherwise be unavailable to plants in certain soils (Altomare et al., 1999; Harman et al., 2004). In addition, another strain of *T. harzianum* TSTh20-1 (Patent Deposit Designation number PTA10317), isolated as an endophytic fungus from a plant that was found growing on oil-sand tailings, was found to promote plant growth, particularly under sub-optimal or stressful conditions with respect to water, organic carbon, nitrogen and mineral content, temperature, and contamination with polycyclic aromatic hydrocarbons or naphthenic acids (PCT Publication No. WO2011/032281).

As described herein, a novel endophytic fungal symbiont *Trichoderma harzianum* strain, referred to herein as ThLm1, was isolated from a grass (*Poacea*) species growing on a beach in Washington state. This strain is not a known pathogen of plants or animals.

When other plants, such as crop plants and native plants, were inoculated with *T. harzianum* strain ThLm1, it was found that this inoculation lead to several benefits including an increase in plant seed germination rates, growth and yields; a decrease in water consumption and NPK (nitrogen, phosphorus and potassium) supplementation; a conference of tolerance to abiotic stresses including drought, temperature, salinity; and an enhancement of general plant health. It was found that ThLm1 was capable of colonizing a broad range of plants including both monocots and eudicots and as such, have cross plant/crop utility. Additionally, it was found that *T. harzianum* strain ThLm1 resided entirely within the plant vegetative tissues and did not grow into seeds or fruits of plants which had been inoculated. As a result, ThLm1 has cross-crop utility, can be used to provide consumer products free of the endophyte, and confers abiotic stress tolerance (salt, temperature, low NPK, drought), biomass and yield enhancement, and increases overall plant health and robustness.

Other strains of *T. harzianum* are commercially used as biopesticides, plant growth enhancers and for the production of industrial enzymes. No strains have been reported to enhance seed germination or confer salinity or temperature stress tolerance, as has been found for ThLm1. Although other strains have been reported to decrease water consumption, ThLm1 produces superior results in agricultural crops and have been shown to confer benefits under field conditions (see Examples).

Accordingly, aspects of the disclosure relate to isolated *Trichoderma harzianum* strain ThLm1, and compositions and methods of use thereof.

Additional aspects of the disclosure relate to methods of use of *Trichoderma harzianum* as described here for strain ThLm1. Provided are methods for increasing stress tolerance by inoculating a plant or a plant seed with an isolated *T. harzianum* fungus or a spore thereof; or a composition comprising the isolated *T. harzianum* fungus or a spore thereof, thereby increasing stress tolerance of the inoculated plant. In some embodiments, the stress is drought, elevated salt, reduced nutrients and/or temperature stress and/or is not the presence of polycyclic aromatic hydrocarbons, napthenic acids, or high pH. Methods for increasing germination of seeds are also provided, in which plant seeds are inoculated with an isolated *T. harzianum* fungus or a spore thereof; or a composition comprising the isolated *T. harzianum* fungus or a spore thereof, thereby increasing germination of the inoculated seeds. Also provided are methods for reducing establishment of fungi other than *T. harzianum* in a plant by inoculating a plant seed or seedling with an isolated *T. harzianum* fungus or a spore thereof; or a composition comprising the isolated *T. harzianum* fungus or a spore thereof, thereby reducing establishment of fungi other than *T. harzianum* in a plant growing from the inoculated seed or seedling. In some embodiments of these aspects, the *T. harzianum* fungus is not strain TSTh20-1 or strain T-22.

Definitions

The term "abiotic stress" as used herein refers to the negative impact of physical and chemical factors on living organisms in a specific environment. Physical and chemical factors can include, but are not limited to, water, organic nutrient levels, mineral nutrient levels, chemical contamination, chemical treatment (e.g., pesticides such as fungicides and insecticides), temperature, rainfall, pH, redox, oxygen content, hydrocarbon residues, alkali, metals, salinity, atmospheric gases, light, soil composition.

The term "endophyte" as used herein refers to a class of fungal symbionts that reside within host plant roots, stems and/or leaves.

The term "inoculating a plant" with a fungus, for example, as used herein refers to applying or infecting a plant with a fungus or any fungal developmental phase.

The term "plant" as used herein includes any member of the plant kingdom that can be colonized by fungi. In one embodiment, the plant is an agricultural crop including, without limitation corn, soybean, rice, wheat, cotton, barley, sorghum, tomato, cucurbits, leafy greens, cotton, berries, woody plants and turf grasses. These plant species have been tested and *T. harzianum* strains such as ThLm1 has been shown to confer growth benefits to them. In other embodiments, the plant is an ornamental, such as Rosaceae, Liliaceae, Azalea, Rhododendron, Poaceae or Chrysanthemum.

The term "progeny of ThLm1" as used herein refers to all cells deriving from ThLm1 cells.

The term "promoting plant growth" or "increased plant biomass and yields" as used herein means that the plant or parts thereof (such as roots and shoots, and seed/fruit yields) have increased in size, mass or number compared to control nonsymbiotic plants, or parts thereof, that has not been inoculated with the fungus or as compared to a predetermined standard.

The term "spores of ThLm1" as used herein refers to asexual reproductive cells formed by ThLm1 fungi, or its sexual stage, *Hypocrea*.

The term "symbiosis" and/or "symbiotic relationship" as used herein refer to a beneficial interaction between two organisms including the interaction most plants have with fungi such as mycorrhizae. Similarly, the term "symbiont" as used herein refers to an organism in a symbiotic interaction.

The term "water use efficiency" as used herein means the amount of water or fluid consumed by plants over a defined period of time. It can also be defined by water or fluid use per gram of plant biomass or water potential.

Isolated *Trichoderma harzianum* ThLm1

In one aspect, the disclosure relates to an isolated *Trichoderma harzianum* strain ThLm1 fungus, submitted to the U.S. Department of Agriculture Culture Collection on Jul. 25, 2013 and deposited under Patent Deposit Designation number NRRL 50846 (date of deposit, Jul. 26, 2013), or a progeny or spore thereof.

A progeny of ThLm1 includes any cell derived from a ThLm1 cell. A spore of ThLm1 includes an asexual reproductive cell formed by ThLm1 fungi, or by its sexual stage, *Hypocrea*. As used herein, "isolated" refers to a cell or fungus that has been removed from its natural symbiotic host. For example, an isolated *Trichoderma harzianum* strain ThLm1 may be removed from a *Poacea* grass species. A fungus may be isolated using methods well-known in the art or described herein. The isolated fungi or cell may be maintained after isolation using methods known in the art, e.g., by culturing on 0.1× potato dextrose agar medium supplemented with ampicillin, tetracycline, and streptomycin, and grown at 22° C. with a 12 hr light regime. After 5-14 days of growth, conidia can be harvested from plates by adding 10 ml of sterile water and gently scraping off spores with a sterile glass slide.

Mutants and variants of ThLm1 can provide the same (or better) benefits than the parent strain. Mutants can be generated using methods known to those skilled in the art, such as by exposure to various chemicals, irradiation, physical conditions, molecular manipulation, viral based DNA modifications and or plasmid based DNA modifications. Mutants can then be selected by the methods described herein to identify mutants that provide the same or better benefits as the parent strain. Variants could also be generated by exposing colonized plants to physical or chemical conditions and selecting for symbiotic benefits.

Compositions

Other aspects of the disclosure relate to compositions comprising a *Trichoderma harzianum* strain, such as ThLm1, and/or a progeny and/or a spore thereof.

In some embodiments, the composition may comprise a physiologically acceptable carrier, such a carrier that is not harmful to a seed and/or plant. Such carriers are known in the art (see, e.g., PCT Publication No. WO96/039844 and U.S. Pat. Nos. 5,586,411; 5,697,186; 5,484,464; 5,906,929;

5,288,296; 4,875,921; 4,828,600; 5,951,978; 5,183,759; 5,041,383; 6,077,505; 5,916,029; 5,360,606; 5,292,507; 5,229,114; 4,421,544; and 4,367,609, each of which is incorporated herein by reference).

In addition, a variety of substances can be added during the treatment of seeds including fungicides, insecticides, nematicides, bactericides, nutrients, biopesticides, other microbial inoculants, colorants, hydration matrices and polymers, all of which are well known in the art. Most of the substances commonly used in seed treatment do not interfere with the establishment of symbioses between *Trichoderma harzianum* strains, such as ThLm1, and plant species.

In some embodiments, the composition is in a fluid form suitable for spray application or dip application. The composition may be diluted or concentrated. In one embodiment, the composition is diluted with water before inoculation. In another embodiment, the composition is in a paste form. In still another embodiment, the composition is in a dry and powdered form for dusting. The composition may be applied to any part of the plant including roots, leaves, stems or seeds. The composition is preferably applied to dried seeds, such as in the form of a seed coating.

One of skill in the art can readily determine the amount or concentration of the composition that may be applied to the plant or plant seed to achieve a desired result, such as induction of stress tolerance and/or enhancement of growth of a plant. In one embodiment, from about 5 to about 100,000 viable spores of the *T. harzianum* strains such as ThLm1 can be used per seed, preferably between about 50 to 1000 viable spores per seed.

Plants and Plant Seeds

Other aspects of the disclosure relate to plants and plant seeds that have been inoculated with an isolated *Trichoderma harzianum* strain, such as ThLm1, or a spore or progeny thereof as described herein. The term "plant" as used herein includes any member of the plant kingdom that can be colonized by fungi. Determining whether a plant is colonized by a *Trichoderma harzianum* strain, such as ThLm1, can be performed using standard methods known to those skilled in the art, such as isolating the fungus from the plant and identifying it (by the methods known in the art, such as described herein), direct DNA extraction from the plant followed by detection analysis (e.g., using PCR or probes). It may be determined that the plant is colonized by simple observation of its health and stress tolerance, or variation in physiological metrics compared to nonsymbiotic plants.

The plant or plant seed may be, e.g., a monocot or a eudicot. In some embodiments, the plant or plant seed is a crop plant or seed thereof, including, without limitation corn, soybean, rice, wheat, watermelon, tomato, cucurbits, peppers, leafy greens, barley, cotton, beans, pea, tubers and woody plants.

In some embodiments, the plant is a native plant. As used herein, a native plant is a plant that is indigenous or naturalized to a habitat or climate zone. Examples of native plants include, but are not limited to grasses, trees, flowering plants, shrubs, and herbs, such as spike bentgrass, annual hairgrass, California brome, slender hairgrass, blue wild rye, meadow barley, American dunegrass, American pokeweed, and Arabidopsis. A person of skill in the art can readily identify native plants for a particular habitat or climate zone, e.g., using known classification systems and databases (see, e.g., the Native Plant Database at wildflower.org; the Native Plant Network at nativeplantnetwork.org; the Plants database through the United States Department of Agriculture; Kenrick, Paul & Crane, Peter R. (1997). The Origin and Early Diversification of Land Plants: A Cladistic Study. Washington, D.C.: Smithsonian Institution Press. ISBN 1-56098-730-8; Raven, Peter H., Evert, Ray F., & Eichhorn, Susan E. (2005). Biology of Plants (7th ed.). New York: W. H. Freeman and Company; and Prance G. T. (2001). "Discovering the Plant World". Taxon (International Association for Plant Taxonomy) 50 (2, Golden Jubilee Part 4): 345-359).

In some embodiments, the plant is a non-native plant. As used herein, a non-native plant is a plant that is not indigenous to a habitat or climate zone and may be naturalized or invasive. Examples of non-native plants include, but are not limited to grasses, trees, flowering plants, shrubs, and herbs, succulents, etc. A person of skill in the art can readily identify native plants for a particular habitat or climate zone, e.g., using known classification systems and databases (see, e.g., the Plants database through the United States Department of Agriculture).

A plant or plant seed may be inoculated using any method known in the art or described herein. A plant may be tested for inoculation with a *T. harzianum* strain, such as ThLm1, or a spore or progeny thereof, e.g., by isolating the fungus from the plant using standard procedures and identifying the fungus by the methods described herein, by direct DNA extraction from the plant followed by detection analysis, or by observation of plant health and stress tolerance, or variation in physiological metrics compared to nonsymbiotic plants.

Methods

Yet other aspects of the disclosure relate to method for promoting stress tolerance and/or enhancing plant growth or seed germination. In some embodiments, the method comprises inoculating a plant or a plant seed with an isolated *Trichoderma harzianum* strain, such as ThLm1, or a spore or progeny thereof.

The term "stress" as used herein refers to the negative impact of physical, organic, and chemical factors on living organisms, such as plants, in a specific environment, including impact on seed germination, plant growth or development, and/or plant (e.g., fruit) yield. Physical and chemical factors can include, but are not limited to, water (including soil moisture and rainfall), nutrient levels (including organic and mineral nutrient levels, and especially low nutrient levels), temperature (including high or low temperatures that are outside of the range of temperatures tolerated by a particular plant or optimal for a particular plant), pH (including high or low pH that are outside of the range of pH tolerated by a particular plant or optimal for a particular plant), Redox, oxygen content, salinity, atmospheric gases, light, and soil composition. Organic factors can include fungi, bacteria, viruses, nematodes or insects which may be pathogenic, or other animals which may be herbivores. As used herein "stress tolerance" refers to resistance of a living organism, such as a plant, to a stress condition. The resistance may be, e.g., an ability to grow or persist in stress conditions that would otherwise result in death of the plant or growth reduction and/or yield reduction in the plant. In some embodiments, the stress tolerance is drought tolerance, salt tolerance, reduced nutrient tolerance, fungal tolerance, and/or temperature tolerance. In some embodiments, plants that are inoculated with *T. harzianum* strains, such as ThLm1, are more stress tolerance relative to plants that are not inoculated with said strains.

An increase or promotion of stress tolerance may be determined by comparing a level of stress tolerance in a plant inoculated with *T. harzianum* strains, such as ThLm1 or a spore or progeny thereof, with a level of stress tolerance in a control plant that has not been inoculated. For example, the growth rate, germination rate, yield, mass, physiological metrics and other such factors may be measured in an inoculated plant under stress conditions, and compared to the same factors in a control non-inoculated plant under similar stress conditions. An increase of one or more such factors in the inoculated plant would indicate an increase or promotion of stress tolerance. An increase or promotion of stress tolerance may also be determined by comparing a level of stress tolerance in a plant inoculated with *T. harzianum* strains, such as ThLm1 or a spore or progeny thereof, with a predetermined standard. The predetermined standard may be, e.g., an average growth rate, germination rate, photosynthetic efficiency, yield or mass of a population of plants, such as a population of non-inoculated plants. In some embodiments, promoting stress tolerance comprises an increase in stress tolerance of at least 5%, 10%, 15%, 20%, 25%, 30%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, or more compared to a control or predetermined standard.

The term "enhancing growth" as used herein refers to a plant or parts thereof (such as roots and shoots) that have an increase in size, extent of root development (e.g., how extensive a root system is), germination rate of seeds, chlorophyll content/level, yield (e.g., number of seeds, or fruit production) or mass compared to control plants, or parts thereof, that has not been inoculated with the fungus or as compared to a predetermined standard. The predetermined standard may be, e.g., an average size, extent of root development, germination rate, chlorophyll content/level, photosynthetic efficiency, yield or mass of a plant or plant part of a population of plants, such as a population of non-inoculated plants. Determining an enhancement in plant growth can be assessed in a number of ways. For example, the size, extent of root development, germination rate, chlorophyll content/level, photosynthetic efficiency, yield or mass of the entire plant or a part thereof (such as seeds, fruit, shoots and roots) can be measured. In some embodiments, enhancing growth comprises increasing size, extent of root development, germination rate, chlorophyll content/level, photosynthetic efficiency, yield or mass of a plant or parts thereof by at least 5%, 10%, 15%, 20%, 25%, 30%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, or more than a control or predetermined standard.

As used herein, "inoculating a plant or plant seed" with a fungus, for example, refers to applying or colonizing a plant or plant seed with a fungus or a fungal cell from any fungal developmental phase, such as a spore. In some embodiments, inoculating the plant comprises colonizing a root and/or stem of the plant with a *Trichoderma harzianum* strain, such as ThLm1.

In some embodiments, a method provided herein further comprises growing the plant or plant seed. The plant or plant seed may be grown in one or more stress conditions, such as drought conditions, high salt conditions, reduced nutrient conditions, low light conditions, parasitic fungal conditions, and/or high temperature conditions.

Thus, in some embodiments, a method provided herein comprises growing the plant or plant seed in soil characterized by high salinity, low moisture, and/or low nutrient content. Soil characterized by high salinity includes soil that has greater than 35 mM amount of a salt, such as Na, Mg, Ca or K chlorides, sulfates or carbonates, present in the soil, such as greater than: 35 mM, 40 mM, 45 mM, 50 mM, 60 mM, 70 mM, 80 mM, 90 mM, 100 mM, 120 mM, 140 mM, 160 mM, 180 mM, 200 mM, 250 mM, 300 mM, 350 mM, 400 mM, 450 mM, 500 mM or more amount of a salt. Soil characterized by low moisture includes soil that has between 0-0.18 in$^3$ water/in$^3$ soil depending on soil type, such as less than: 0.18, 0.17, 0.16, 0.15, 0.14, 0.13, 0.12, 0.11, 0.10, 0.09, 0.08, 0.07, 0.06, 0.05, 0.04, 0.03, 0.02 or 0.01 in$^3$ water/in$^3$ soil. Soil characterized by low nutrient content includes soil that has fewer than 80 lbs/acre of nutrient (comprising 20% each of nitrogen, phosphorus, and potassium (NPK), and associated micronutrients), such as fewer than: 75, 70, 65, 60, 55, 50, 45, 40, 35, 30, 25, 20, 15, 10 or 5 lbs/acre of nutrient.

In some embodiments, a method provided herein comprises growing the plant or plant seed at an average temperature at or above 36 degrees Celsius, such as 36, 37, 38, 39, 40, 41, 42, 43, 44, 45, 46, 47, 48, 49, 50 or higher. In some embodiments, the method comprises germinating the plant seed at an average temperature at or above 36 degrees Celsius, such as 36, 37, 38, 39, 40, 41, 42, 43, 44, 45, 46, 47, 48, 49, 50 or higher.

In some embodiments, a method provided herein comprises growing the plant or plant seed at an average temperature at or below 15 degrees Celsius, such as 15, 14, 13, 12, 11, 10, 9, 8, 7, 6, 5 or lower. In some embodiments, the method comprises germinating the plant seed at an average temperature at or below 15 degrees Celsius, such as 15, 14, 13, 12, 11, 10, 9, 8, 7, 6, 5 or lower.

In some embodiments of any of the methods provided herein, the plant or plant seed is a crop plant or crop plant seed. In some embodiments, the crop plant or crop plant seed is watermelon, tomato, corn, wheat, soybean, cucurbits, peppers, leafy greens, barley, cotton, beans, pea, tubers, woody plants, berries or rice, or a seed thereof. In other embodiments, the plant or plant seed is an ornamental, such as Rosaceae, Liliaceae, Azalea, Rhododendron, Poaceae or Chrysanthemum.

Unless defined otherwise, all technical and scientific terms used herein are intended to have the same meaning as is commonly understood by one of ordinary skill in the relevant art.

As used herein, the singular forms "a," "an", and "the" include the plural reference unless the context clearly dictates otherwise.

All publications and patent applications cited in this specification are herein incorporated by reference as if each individual publication or patent application were specifically and individually indicated to be incorporated by reference.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Isolation and Identification of ThLm1 as a Beneficial Symbiont

Isolation and Inoculation of ThLm1

*Trichoderma harzianum* strain ThLm1 was isolated from a grass (*Poacea*) species growing on a beach in Washington state. The habitat-stresses on these plants were identified as drought, low soil nutrients, and elevated salinity. *Leymus mollis* (dunegrass) plants were collected from several coastal beach habitats in the San Juan Island Archipelago, Wash. Plants were washed until soil debris was removed, placed into plastic zip-loc baggies and surface sterilized as previously described (Redman et al., 2001, 2002a). Using aseptic technique, plants were cut into sections representing the roots, rhizomes and stems, plated on fungal growth media [0.1×PDA (potato dextrose agar)] and incubated at room temperature for 5-7 days under cool fluorescent lights to allow for the emergence of fungi. Upon emergence, 30 representative isolates of the dominant fungal endophyte represented (×95%) were sub-cultured and, of these, single spore isolation of 10 representative isolates was performed as previously described (Redman et al., 1999). All 10 of the representative isolates were placed under sterile water supplemented with 50-100 mg/ml of ampicillin in sterile 1.5 ml screw-cap tubes and placed at 4° C. for long-term storage.

Colonization of Seeds and Plants with ThLm1

Several test plants were inoculated with ThLm1. Corn (*Zea mays*) and soybean (*Glycine max*) seeds were surface-sterilized in a 0.5-1.0% (v/v) sodium hypochlorite solution for 15-20 min with moderate agitation and rinsed with 10-20 volumes of sterile distilled water. These plant species represent two major plant lineages monocots and eudicots. However, ThLm1 also establishes symbioses with many other plants including vegetables (e.g., tomato, cucurbits, peppers, pea, beans, turf, leafy greens etc.), staple crops (e.g., wheat, rice, barley, tubers), grasses and woody plants, which are treated as described for corn and soybean to colonize with ThLm1. Plants can establish symbioses with ThLm1 by treating (sprayed, soaked, mixed or watered) seeds, germlings, seedlings or older stage plants directly with either liquid or powdered formulations of spores (10-10,000 spores/seed). Spores can be applied to any part of the plant with best results obtained by inoculating lower stem and roots.

ThLm1 was found to establish symbiosis with many plant species inoculated with ThLm1 including crop plants and native plants. Inoculation with ThLm1 was found to confer stress tolerance. A summary of the plants that were inoculated with ThLm1 and had improved stress tolerance are shown in Table 2.

ThLm1 Increased Plant Growth and Health in the Absence of Stress

Corn plants were inoculated or not inoculated with ThLm1 and were grown in the absence of stress conditions in a greenhouse for one month. The corn plants were then separated into root and shoot sections for wet weight measurements. Statistical analysis of the weight measurements showed that plants inoculated with ThLm1 (symbiotic with ThLm1) were significantly larger than non-inoculated plants (ANOVA, $P<0.05$, FIG. 1).

Figure 2:
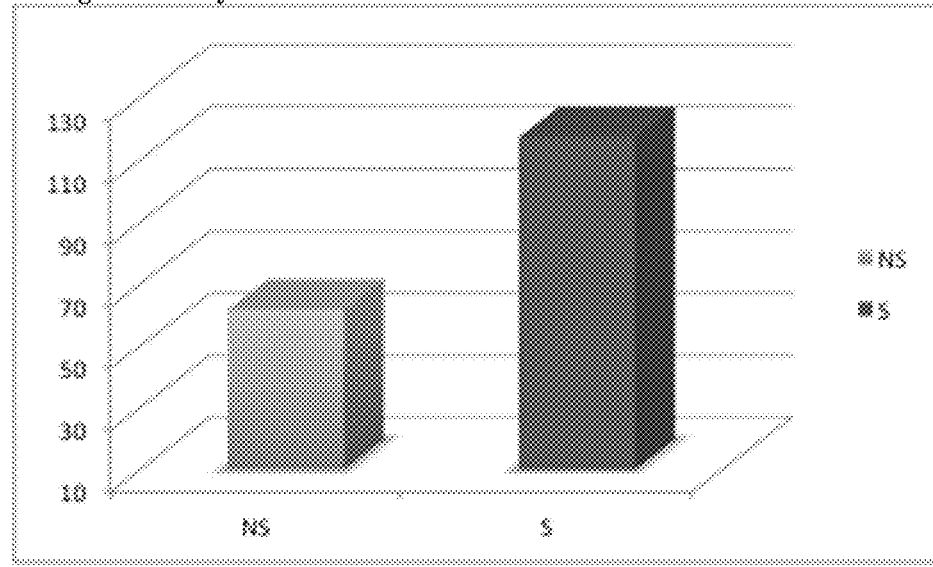
FIG. 2 is a bar graph depicting corn growth and yield enhancement through symbiosis with ThLm1. Left=Nonsymbiotic (NS), Right=Symbiotic (S) with ThLm1. Values on the Y-axes are wet weights in grams (g) with average weights shown.

Corn growth and yield were also measured in corn plants inoculated or not inoculated with ThLm1. Mature greenhouse plants were further grown in the absence of stress to produce corn ears (yields) for wet weight measurements. Statistical analysis showed that plants inoculated with ThLm1 (symbiotic with ThLm1) produced significantly more yield than non-inoculated plants (N=48; $P>0.05$, FIG. 2).

Figure 3:
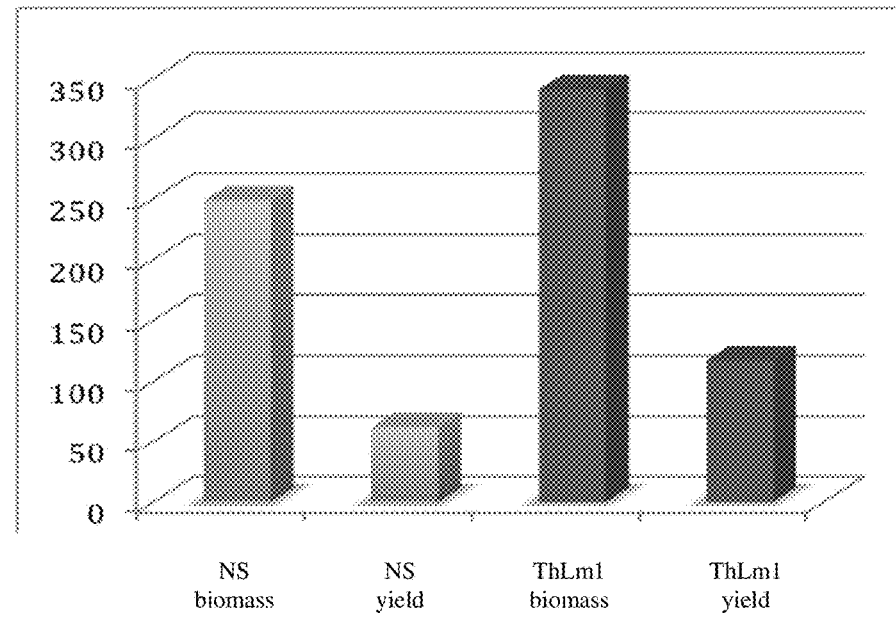
FIG. 3 is a graph showing corn growth and yield enhancement through symbiosis with ThLm1. Left two bars=Nonsymbiotic (NS), Right two bars=Symbiotic (S) with ThLm1. Values on the Y-axes are wet weights in grams (g) with average weights shown.
Figure 4:
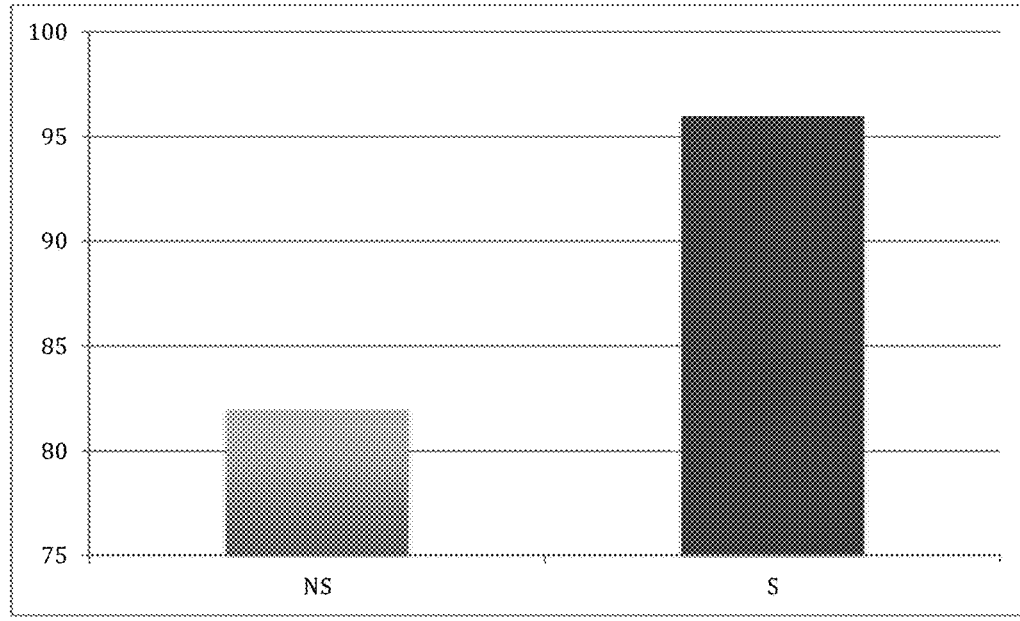
FIG. 4 is a bar graph depicting seed germination of corn symbiotic with ThLm1(S) or nonsymbiotic (NS). Left=Nonsymbiotic (NS), Right=Symbiotic (S) with ThLm1. Values on the Y-axes represent percent seed germination with average values shown.

Corn growth and yield enhancement in ThLm1 inoculated corn grown in the absence of stress was further measured. Mature greenhouse plants grown in the absence of stress were separated into whole plant weight (biomass) or corn ears (yields) for wet weight measurements. Statistical analysis showed that plants inoculated with ThLm1 (symbiotic with ThLm1) were significantly larger than non-inoculated plants (N=48; $P>0.05$, FIG. 3).

Seed germination enhancement in ThLm1 inoculated plants was also measured. Germination of corn seeds was measured in the presence and absence of stress in plant growth incubators and greenhouses. Statistical analysis showed that seeds inoculated with ThLm1 (symbiotic with ThLm1) had significantly higher rates of germination than non-inoculated (NS) seeds (N=100; SD<5; $P<0.05$, FIGS. 4, 22-25).

Figure 5:
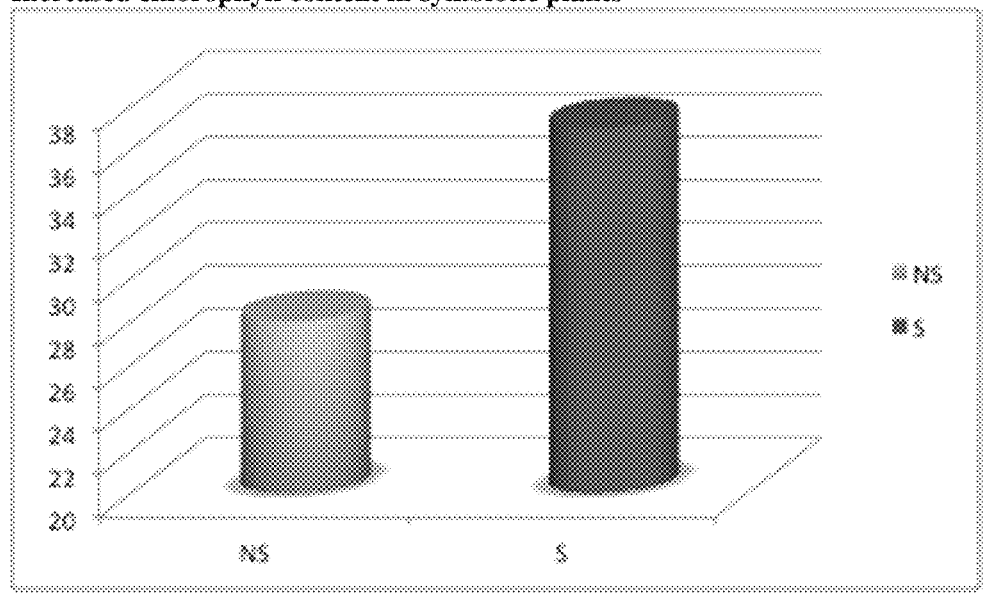
FIG. 5 is a graph depicting increased chlorophyll content in symbiotic corn plants. Left=Nonsymbiotic (NS), Right=Symbiotic (S) mature greenhouse grown corn plants in the absence of stress were measured for chlorophyll content (Y-axis, numbers are SPAD values) with average values shown.
Figure 13:
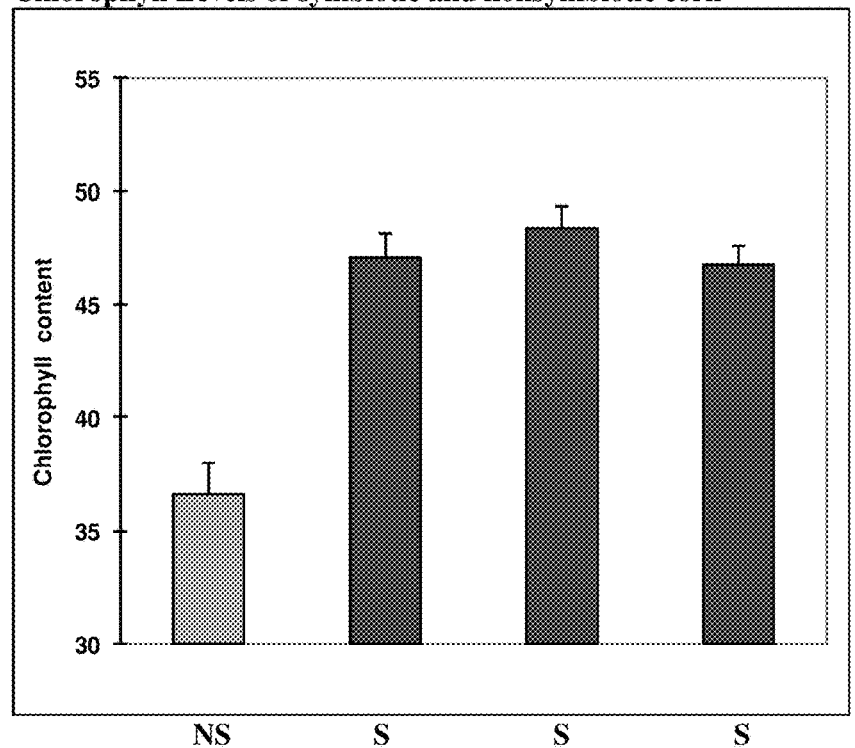
FIG. 13 is a bar graph depicting leaf chlorophyll content of corn plants. SPAD measurements were taken which indicated relative % chlorophyll. Each of the three "S" bars represent three unique preparations of ThLm1.
Figure 14:
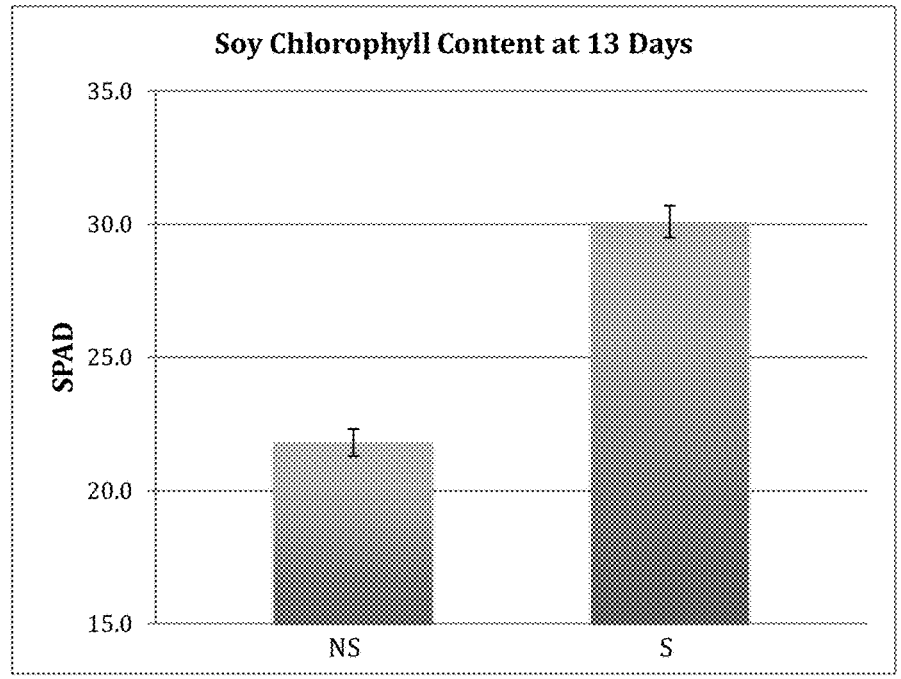
FIG. 14 is a bar graph of SPAD measurements of soybean plants symbiotic (S, right bar) with ThLm1 or nonsymbiotic (NS, left bar). SPAD measurements indicated the relative % of chlorophyll in plants.

Chlorophyll content was also measured in ThLm1 inoculated plants. Mature greenhouse corn plants grown in the absence of stress were measured for % chlorophyll content. Statistical analysis showed that ThLm1 inoculated plants (symbiotic with ThLm1) had higher chlorophyll content than non-inoculated plants (N=9; $P>0.05$, FIGS. 5, 13, 14). As a general observation, ThLm1 inoculated plants looked greener and more robust than non-inoculated plants.

TABLE 2

| Plants inoculated with ThLm1 | | | | |
| --- | --- | --- | --- | --- |
| | Common Name | Colonization | Effect on Plants | Interaction |
| Crop Species | | | | |
| *Citrullus lanatus* subsp. *vulgaris* | watermelon | roots, stem | stress tolerance | mutualism |
| *Solanum tycopersicum* | tomato | roots, stem | stress tolerance | mutualism |
| *Zea mays* subsp. *mays* | corn | roots, stem | stress tolerance | mutualism |
| *Triticum aestivum* | wheat | roots, stem | stress tolerance | mutualism |
| *Glycine max* | soybean | roots, stem | stress tolerance | mutualism |
| *Oryza sativa* | rice | roots, stem | stress tolerance | mutualism |
| Native Species | | | | |
| *Agostis exarata* | spike bentgrass | roots, stem, leaf | stress tolerance | mutualism |
| *Deschampsia danthonioides* | annual hairgrass | roots, stem, leaf | stress tolerance | mutualism |
| *Bromus carinatus* | california brome | roots, stem, leaf | stress tolerance | mutualism |
| *Deschampsia elongata* | slender hairgrass | roots, stem, leaf | stress tolerance | mutualism |
| *Elymus glaucus* Buckley | blue wild rye | roots, stem, leaf | stress tolerance | mutualism |
| *Hordeum brachyantherum* Nevski | meadow barley | roots, stem, leaf | stress tolerance | mutualism |
| *Leymus mollis* | American dunegrass | roots, stem, leaf | stress tolerance | mutualism |
| *Phytoiocca americana* | American pokeweed | roots, stem, leaf | stress tolerance | mutualism |
| *Arabidopsis thaliana* | *Arabidopsis* | roots, stem, leaf | stress tolerance | mutualism |

These data show that ThLm1 inoculation of plants generally increased plant health, including plant growth, yield, germination rates, and chlorophyll content in the absence of stress.

ThLm1 Increased Plant Growth and Health in the Presence of Stress

Figure 6A:
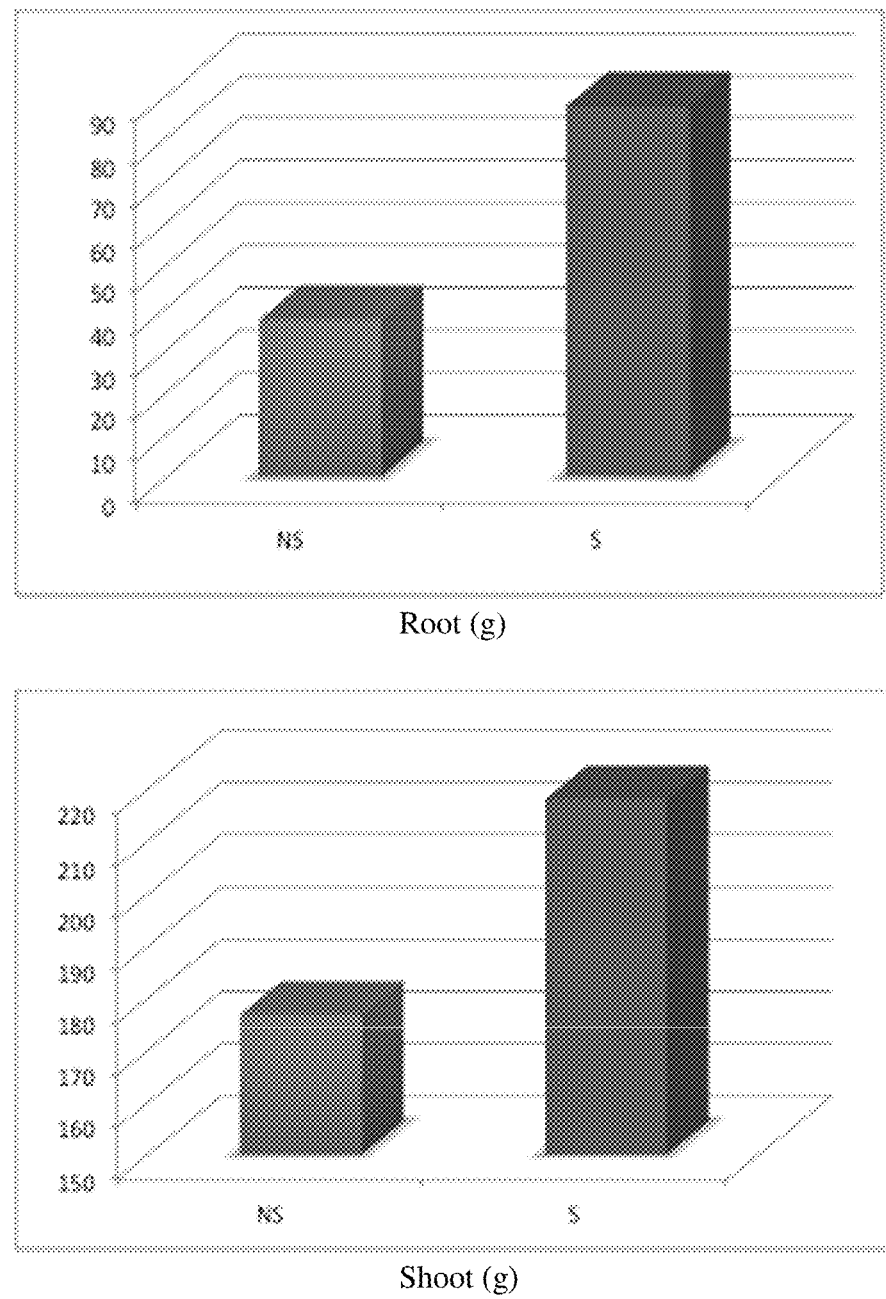
FIG. 6A is a series of bar graphs showing root and shoot weight of corn plants exposed to drought stress. Left bars of each graph=Nonsymbiotic (NS), Right bars of each graph=Symbiotic (S) with ThLm1. Values on the Y-axes are wet weights in grams (g) with average weights shown.

Stress conditions were also tested to determine if plants inoculated with ThLm1 were healthier than plants not inoculated with ThLm1. Root and shoot weights were measured in corn plants exposed to drought stress that were previously inoculated or not inoculated with ThLm1. Sixty-day old corn plants were exposed to no stress (watered fully every 2 days), moderate drought stress (watered every 4 days) or high drought stress (watered every 7 days). Plants were then assessed for biomass from high drought exposed plants (roots and shoots). Plants were separated into root and shoot sections for wet weight measurements. Statistical analysis showed that plants inoculated with ThLm1 (symbiotic with ThLm1) were significantly larger than non-inoculated plants (N=36; P>0.05, FIG. 6A).

Figure 6B:
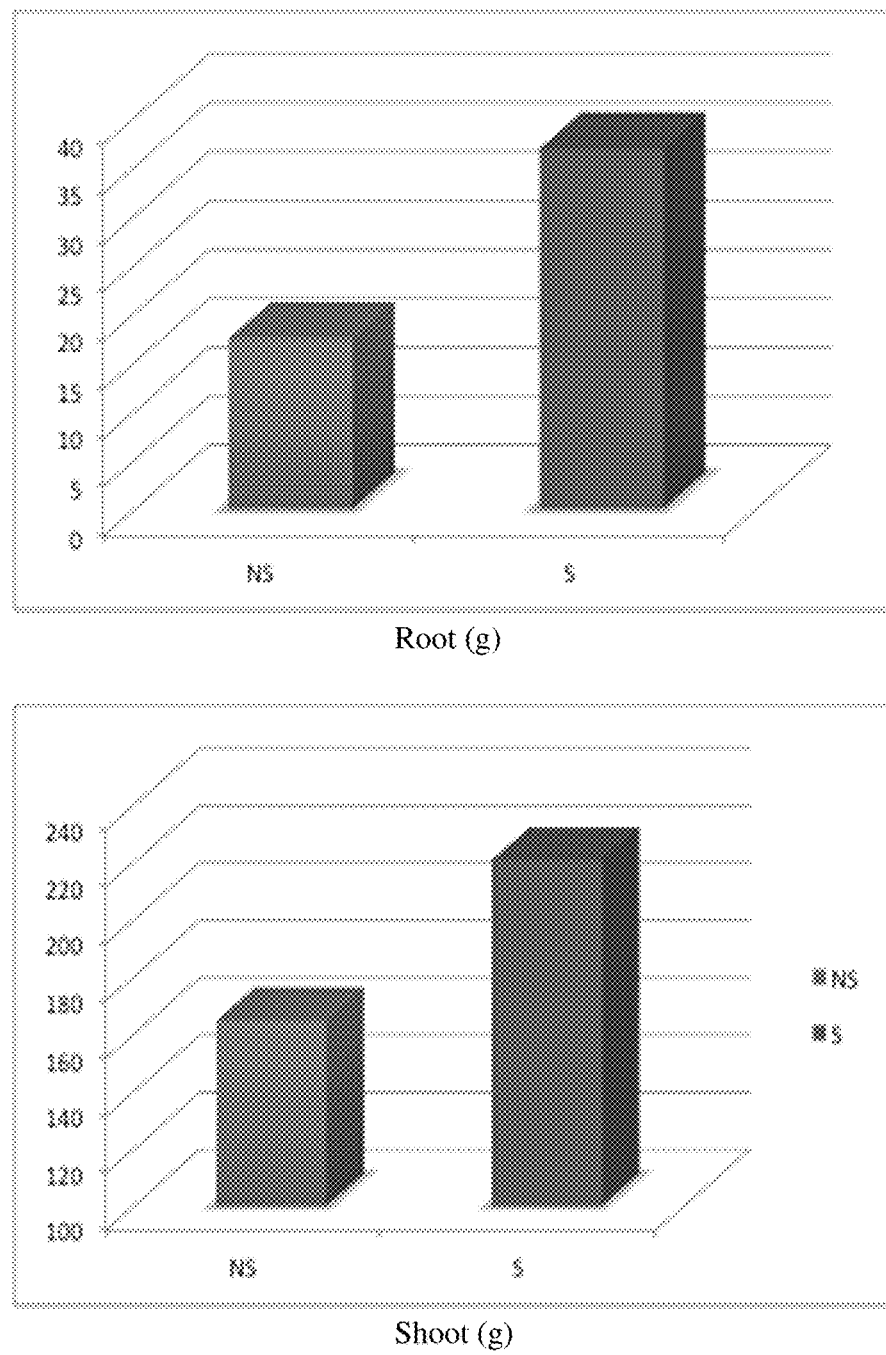
FIG. 6B is a bar graph showing root and shoot weight of corn plants exposed to low nutrient stress. Left bars of each graph=Nonsymbiotic (NS), Right bars of each graph=Symbiotic (S) ThLm1. Values on the Y-axes are wet weights in grams (g) with average weights shown.

Root and shoot measurements were also taken in corn plants exposed to low nutrient stress that were previously inoculated or not inoculated with ThLm1. One-week old corn plants were given an initial watering with nutrients (nitrogen, phosphorus & potassium based plant fertilizer, NPK), after which plants were exposed every 2 days to no nutrient stress (watered with full strength NPK) or low nutrient stress (watered with ¼ strength NPK) for the duration of the experiments (approximately 90 days). Plants were then assessed for biomass (roots and shoots). Plants were separated into root and shoot sections for wet weight measurements. Statistical analysis showed that plants inoculated with ThLm1 (symbiotic with ThLm1) were significantly larger than non-inoculated plants (N=36; P>0.05, FIG. 6B).

Figure 7:
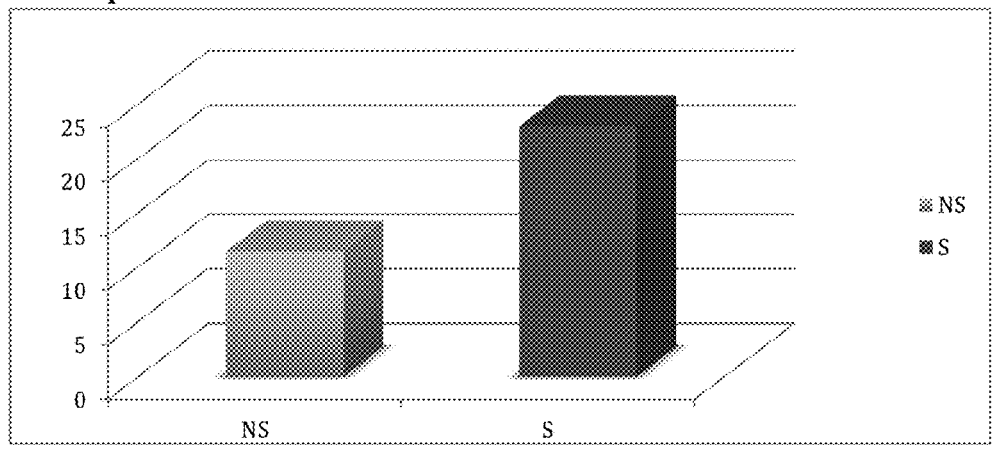
FIG. 7 is a bar graph depicting the weight of corn exposed to salt stress. Left=Nonsymbiotic (NS), Right=Symbiotic (S) with ThLm1. Numbers on the Y-axis are wet weight in grams with average weights shown.

Weight measurements were taken in corn plants under salt stress that were previously inoculated or not inoculated with ThLm1. Sixty-day old plants were exposed every 2 days to no salt stress (water with standard levels of NPK) or salt stress (200 mM NaCl in standard NPK solution) for thirty days. Plant wet weights were measured. Statistical analysis showed that plants inoculated with ThLm1 (symbiotic with ThLm1) were significantly larger than non-inoculated plants (N=36; P≥0.05, FIG. 7).

Figure 8:
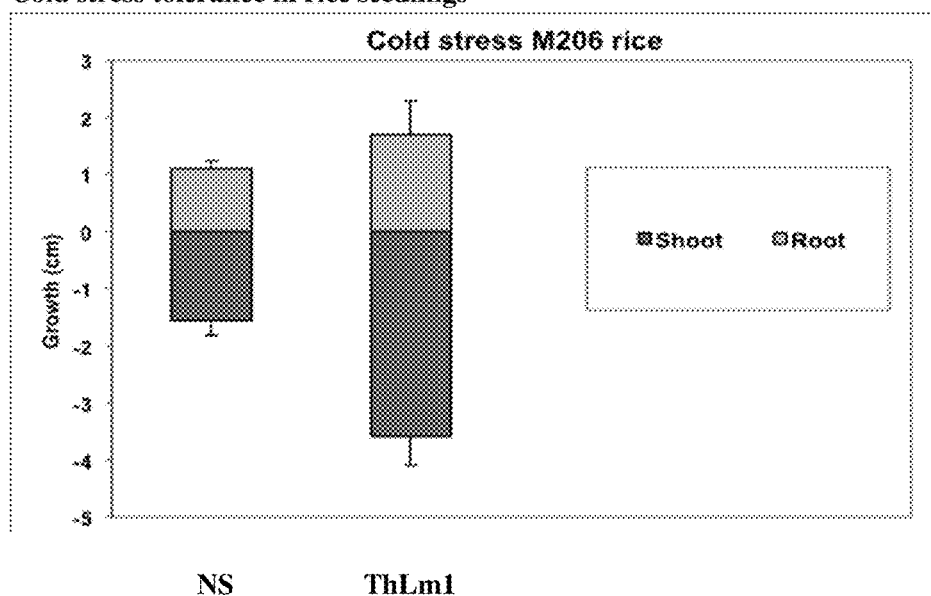
FIG. 8 is a graph depicting cold stress tolerance in rice seedlings. Root biomass is depicted by the upper half of each bar. Root and shoot growth are shown (cm). Shoot growth is depicted by the lower half of each bar.

Cold stress tolerance was measured in rice seedlings that were previously inoculated or not inoculated with ThLm1. The rice seedlings were exposed to cold-water stress. After 2 weeks, rice seedlings were assessed for root and shoot biomass (wet g). Rice inoculated with ThLm1 had statistically larger roots and shoots (N=10; P<0.05, FIG. 8).

Figure 9:
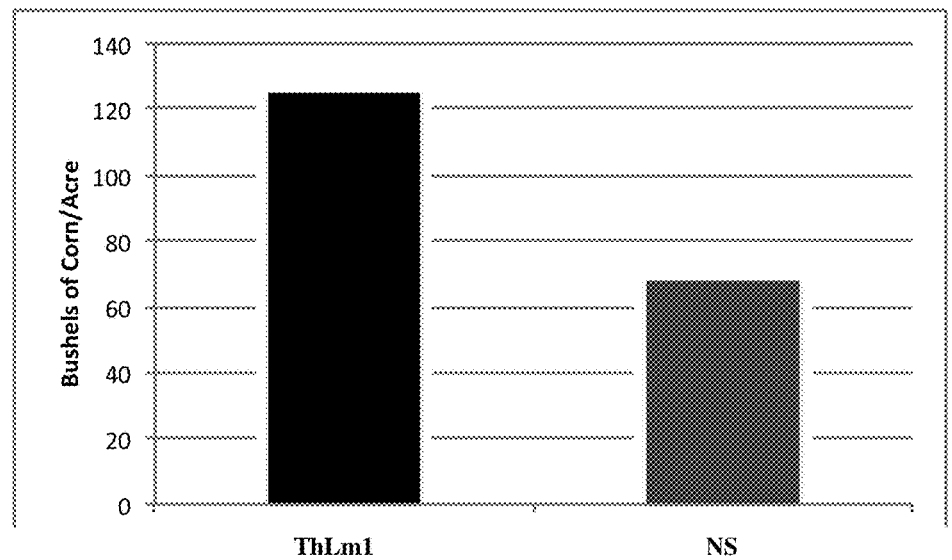
FIG. 9 is a graph depicting field evaluation under drought stress. Yield data is shown for five replicate plots containing 120 corn plants each. Plants symbiotic with ThLm1 produced an average of 85% more yield than nonsymbiotic (NS) plants.

A field evaluation under drought stress was also conducted. Plants were grown under dryland cultivation in Michigan, USA, and exposed to the worst drought in 50 years. Yield data was obtained for four replicate plots containing 120 corn plants each. Plants inoculated with ThLm1 (symbiotic with ThLm1) produced an average of 85% more yield than non-inoculated plants, FIG. 9.

These data show that inoculation with ThLm1 improved plant health, such as growth and yield, under stress conditions including drought, low nutrient, temperature, and salt stress.

SUMMARY

Taken together, the data show that inoculation with ThLm1 increased seed germination rates and seedling growth, conferred tolerance to various stresses (salt, temperature, drought, nutrients), enhanced general robustness and health (such as an increase in % chlorophyll), and increased yields. In addition, it was found (data not shown) that ThLm1 could competitively out compete plant colonization by other microbes and in so doing, thwart the ingress of pathogenic organisms (thereby decreasing incidence of disease) in a wide range or agricultural plants such as soybean, rice and corn. A list of benefits that ThLm1 provided to plants upon inoculation is summarized in Table 3.

TABLE 3

| Th-Lm1 Inoculated Plant benefits Inoculated Plant Characteristics |
| --- |
| Improved seed germination |
| Drought tolerance |
| Salt tolerance |
| Temperature tolerance |
| Decreased nutrient requirements |
| Increased photosynthetic efficiency |
| Increased chlorophyll content |
| Field benefits conferred in corn, rice, wheat, barley, soybean |
| Prevent colonization by other fungi |
| Decreased water consumption |
| Enhanced plant growth |

Example 2. Isolation and Inoculation of Plants with ThLm1

Isolation of ThLm1

To isolate ThLm1, plants were washed until soil debris was removed, placed into plastic Zip-loc baggies and surface sterilized as previously described (Redman et al., 2001, 2002a). Using aseptic technique, plants were cut into sections representing the roots, rhizomes and stems, plated on fungal growth media [0.1×PDA (potato dextrose agar, Difco)] and incubated at room temperature for 5-7 days under cool fluorescent lights to allow for the emergence of fungi. Upon emergence, 30 representative isolates of the dominant fungal endophyte represented were sub-cultured and, of these, single spore isolation of 10 representative isolates was performed as previously described (Redman et al., 1999). All 10 of the representative isolates were placed under sterile water supplemented with 50-100 mg/ml of ampicillin in sterile 1.5 ml screw-cap tubes and placed at 4° C. for long-term storage.

Culturing ThLm1:

ThLm1 was cultured on 0.1× potato dextrose agar (PDA) medium (Difco). The medium was supplemented with 50-100 ug/ml of ampicillin, tetracycline, and streptomycin, and fungal cultures grown at 22° C. with a 12 hr light regime. After 5-14 days of growth, conidia were harvested from plates by adding 10 ml of sterile water and gently scraping off spores with a sterile glass slide. The final volume of spores was adjusted to 100 ml with sterile water, filtered through four layers of sterile cotton cheesecloth gauze and spore concentration adjusted to $10^4$-$10^5$ spores/ml.

Identification of ThLm1:

Fungi were identified using conidiophore and conidial morphology (Arx, 1981; Barnett and Hunter, 1998; Leslie and Summerell, 2005). Once isolates from *L. mollis* were identified as the same fungal species microscopically, three of the isolates were randomly selected for molecular species identification. Species designations were based on sequence analysis of the variable ITS1 and ITS2 sequences of rDNA [ITS4 (5'-tcctccgcttattgatatgc-3'; SEQ ID NO:1)/ITS5 (5'-ggaagtaaaagtcgtaacaagg-3'; SEQ ID NO:2) primers] and translation elongation factor [EF1T (5'-atgggtaaggagga-caagac-3'; SEQ ID NO:3)/EF2T (5'-ggaagtaccagtgatcatgtt-3'; SEQ ID NO:4) and EF11 (5'-gtggggcatttaccccgcc-3'; SEQ ID NO:5)/EF22 (5'-aggaaccctaccgagctc-3'; SEQ ID NO:6) primers (O'Donnell et al., 2000; White et al., 1990)]. DNA was extracted from mycelia and PCR amplified as previously described (Rodriguez, 1993; Rodriguez and Yoder, 1991). PCR products were sequenced and BLAST searched against the GenBank database. Morphological and GenBank analysis identified the three isolates/species as the same species (*Trichoderma harzianum*) and all isolates tested for plant benefits.

Benefits of *Trichoderma harzianum* strain ThLm1

A series of studies were performed to assess the benefits of *Trichoderma harzianum* strain ThLm1 on a monocot (corn) and eudicot (soy and/or tomato) to demonstrate that the fungus establishes a beneficial symbiosis with plants of both lineages.

ThLm1 Increased Plant Growth and Health in the Absence of Stress

Firstly, experiments were performed in the without stress conditions to determine the general plant health, such as plant growth and development, of ThLm1 inoculated plants in the absence of stress.

Figure 10:
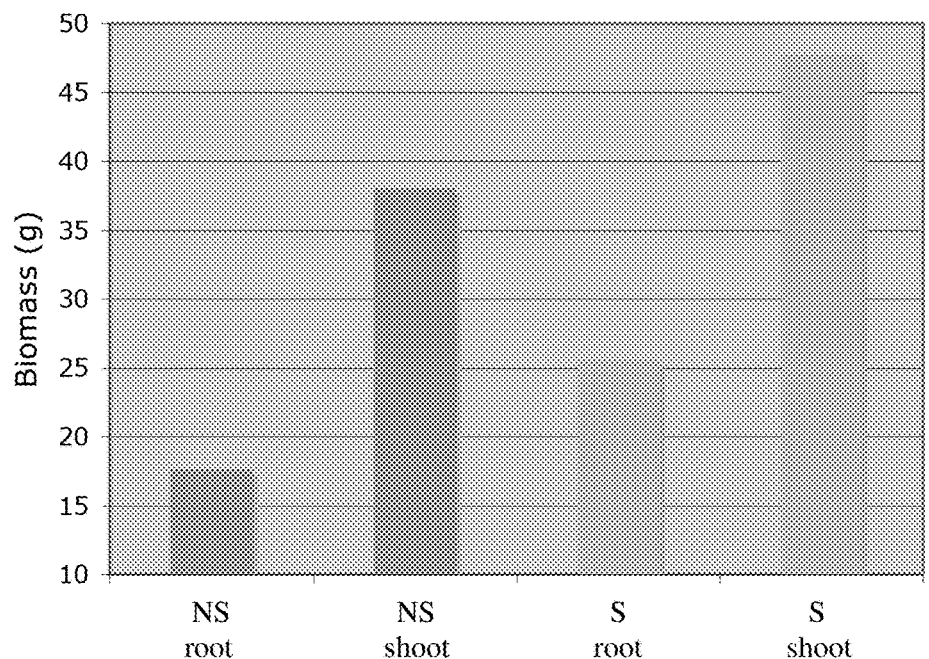
FIG. 10 is a graph showing shoot and root biomass of corn either nonsymbiotic (NS) or symbiotic (S) with ThLm1. Values on the Y-axes are fresh weight biomass in grams (g).
Figure 11:
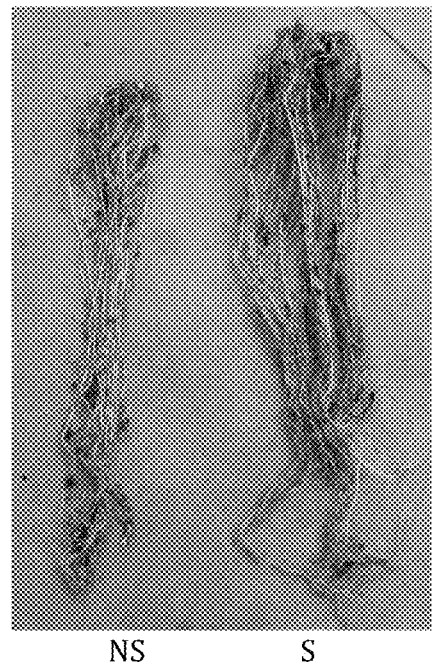
FIG. 11 is a photograph showing that symbiotic corn plants inoculated with ThLm1 produced more extensive root systems with more lateral roots.

Corn seedlings inoculated or not inoculated with ThLm1 were assessed for shoot and root biomass after 12 weeks of growth. Growth enhancement was observed in plants inoculated with ThLm1 (N=48; SD<6.8; P<0.050, FIG. 10). Additionally, the corn inoculated with ThLm1 was found to produce a more extensive root system with more lateral roots (FIG. 11).

Figure 12:
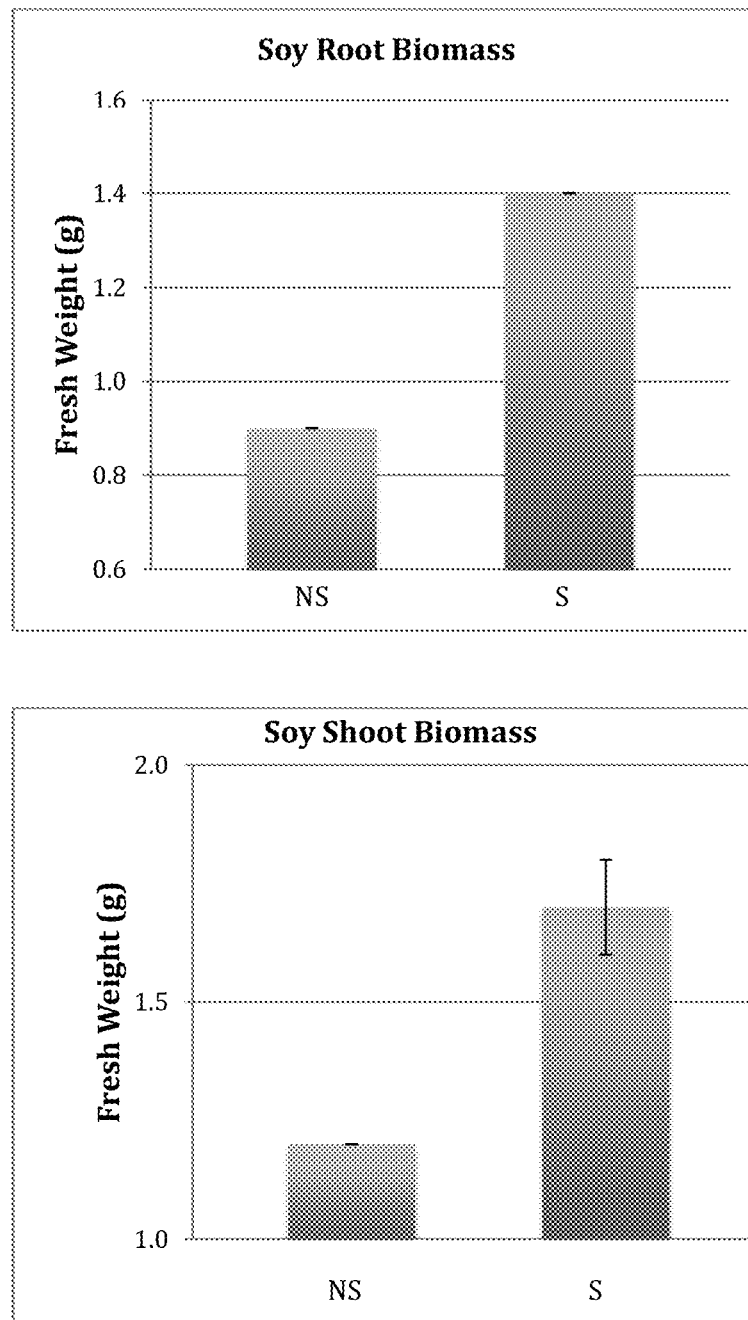
FIG. 12 is a bar graph showing root and shoot biomass of soybeans either nonsymbiotic (NS) or symbiotic (S) with ThLm1. Values on the Y-axes are fresh weight biomass in grams (g).

Soybeans seedlings inoculated or not inoculated with ThLm1 were also assessed for shoot and root biomass after 13 days of growth. Growth enhancement of soybean seedlings was observed in plants inoculated with ThLm1 (N=10; SD<10%; P<0.050, FIG. 12).

Corn plants inoculated or not inoculated with ThLm1 were assessed for chlorophyll content. SPAD measurements were taken which indicated relative % chlorophyll. Corn plants inoculated with ThLm1 were found to have a higher chlorophyll content than non-inoculated plants (N=60, P<0.05, FIG. 13). Generally, corn plants inoculated with ThLm1 were darker green than non-inoculated plants.

Soybean plants inoculated or not inoculated with ThLm1 were also assessed for chlorophyll content. Soybean plants inoculated with ThLm1 had significantly more chlorophyll than non-inoculated plants (N=10, SD<5%, P<0.05, FIG. 14).

Corn seeds inoculated or not inoculated with ThLm1 were assessed for germination. Corn seeds inoculated with ThLm1 had a higher % of germination (N=100; SD<5; P<0.05, FIG. 4).

Figure 15:
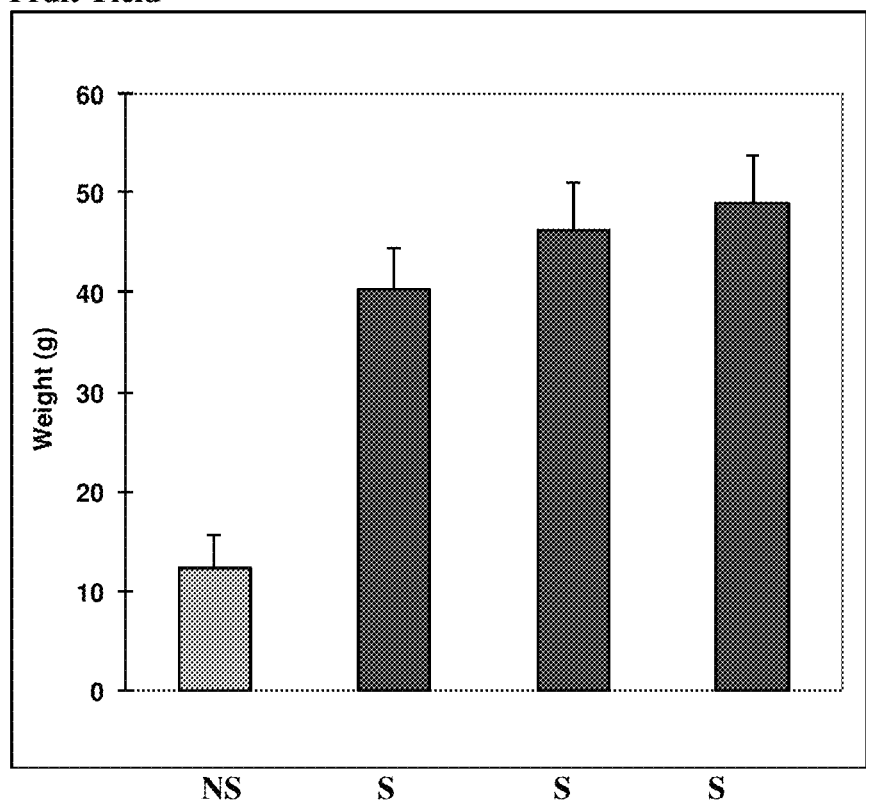
FIG. 15 is a bar graph showing fruit yield of corn symbiotic with different preparations of ThLm1 (S) or nonsymbiotic (NS).

Corn plants inoculated or not inoculated with ThLm1 were assessed for fruit yield. For corn yield assessment, 6 corn plants were pooled to determine yield weights of ears. ThLm1 inoculated plants produced more fruit than non-inoculated plants (N=6, P<0.05, FIG. 15).

Together, these data show that in the absence of stress ThLm1 inoculation conferred growth enhancement, more extensive root systems, increased chlorophyll levels, higher germination rates, and higher fruit yields.

ThLm1 Increased Plant Growth and Health in the Presence of Stress

Next, experiments were performed under stress conditions to determine the general plant health of ThLm1 inoculated plants in the presence of stress.

Figure 16:
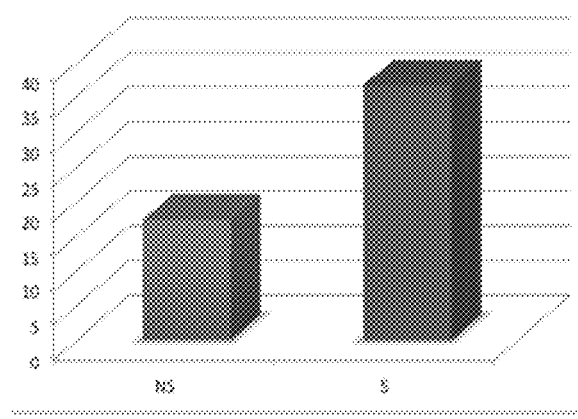
FIG. 16 is a series of bar graphs depicting the roots, shoots, and yield of corn plants symbiotic with ThLm1 (S, right bars in each graph) or nonsymbiotic (NS, left bars in each graph) under low nutrient stress.
Figure 16:
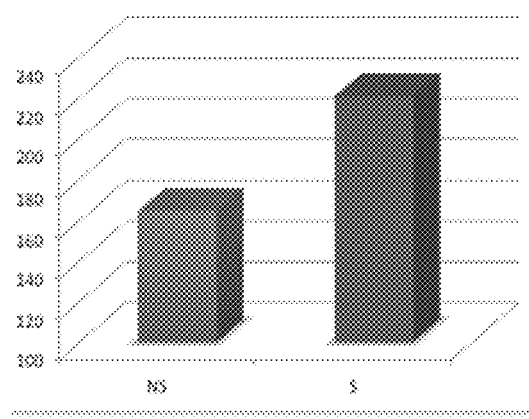
Figure 16:
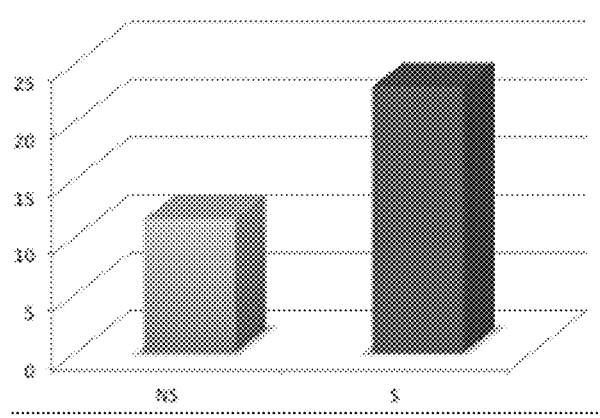

Corn plants inoculated or not inoculated with ThLm1 were assessed for root mass, shoot mass, seedling weight, and yield under low nutrient stress. One-week old corn plants were given an initial watering with nitrogen, phosphorus, potassium (NPK), after which plants were exposed every 2 days to no NPK stress (watered with full strength NPK), low NPK stress (watered with ½ strength NPK), or high NPK stress (watered with ¼ strength NPK) for the duration of the experiments (approximately 90 days). Plants were then assessed for yields and biomass (roots and shoots). ThLm1 inoculated plants had higher root mass, shoot mass, seedling weight, and yields than non-inoculated plants under low nutrient stress (N=12-60; SD<10%, P<0.05, FIG. 16).

Figure 17:
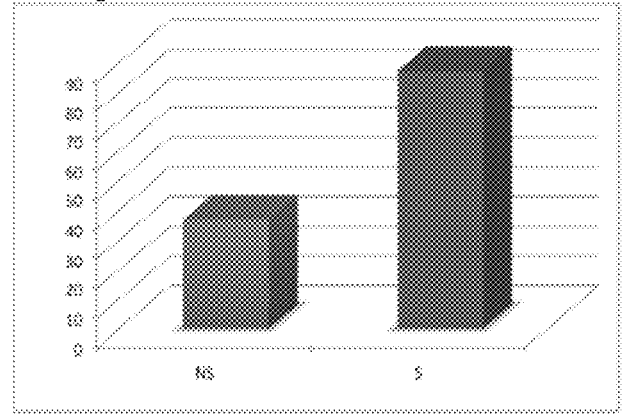
FIG. 17 is a series of bar graphs depicting the roots, shoots, and yield of corn plants symbiotic with ThLm1 (S, right bars in each graph) or nonsymbiotic (NS, left bars in each graph) under drought stress.
Figure 17:
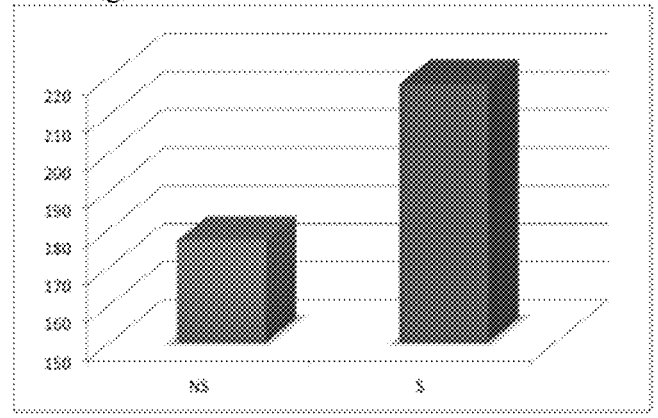
Figure 17:
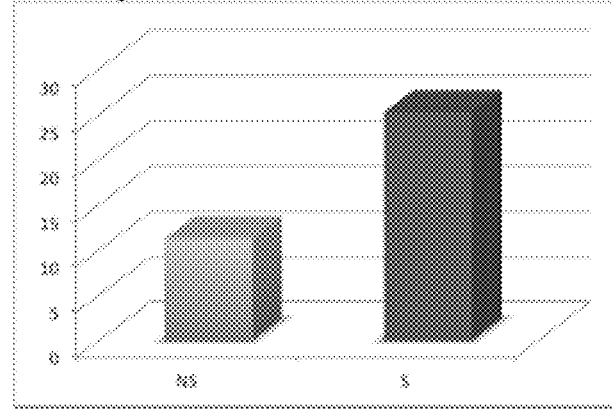

Corn plants inoculated or not inoculated with ThLm1 were assessed for root mass, shoot mass, and yield under drought stress. Sixty-day old corn plants were exposed to no stress (watered fully every 2 days) or high drought stress (watered every 7 days). Plants were then assessed for yields and biomass (roots and shoots). ThLm1 symbiotic plants had higher root mass, shoot mass, and yields than NS plants under drought stress (N=12-60; SD<10%, P≤0.05, FIG. 17).

Figure 18:
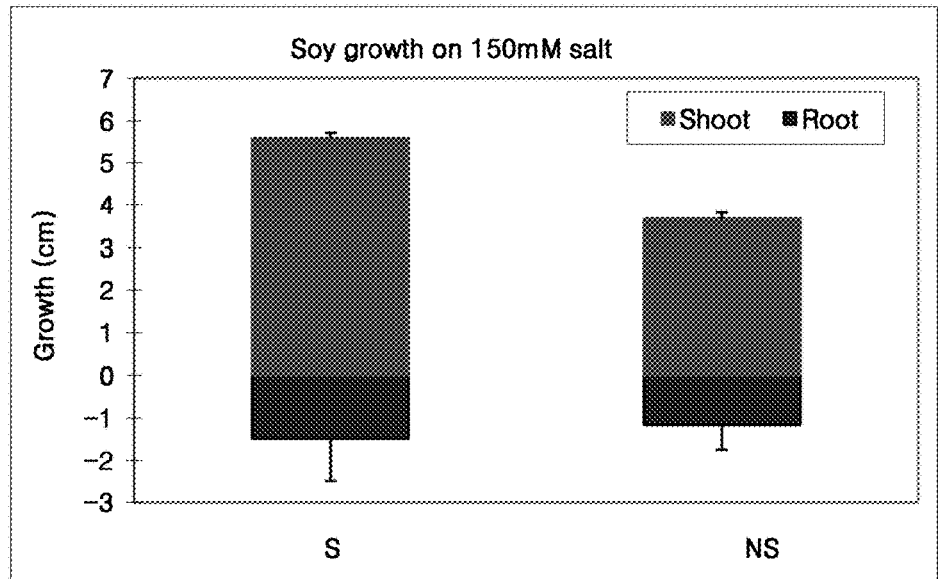
FIG. 18 is a bar graph depicting root and shoot biomass in soybean plants symbiotic with ThLm1 (S, left bar) or nonsymbiotic (NS, right bar) under salt stress.

Soybean plants inoculated or not inoculated with ThLm1 were assessed for root and shoot biomass under salt stress. Eight inoculated and eight non-inoculated seedlings were exposed to salt (300 mM) for two weeks. Inoculated plants produced significantly more shoot and root biomass (FIG. 18). Non-inoculated plants leaves were wilted at the end of the study while inoculated plants remained healthy.

Figure 19:
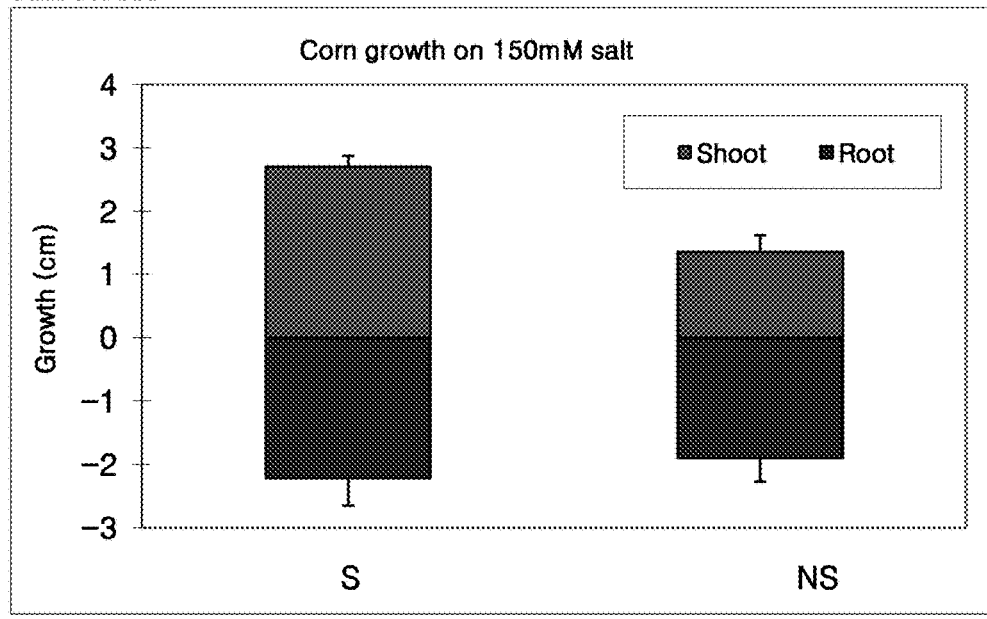
FIG. 19 is a bar graph depicting shoot and root biomass in corn symbiotic with ThLm1 (S, left bar) or nonsymbiotic (NS, right bar) under salt stress.

Corn plants inoculated or not inoculated with ThLm1 were assessed for root and shoot biomass under salt stress. Eight inoculated and eight non-inoculated seedlings were exposed to salt (300 mM) for two weeks. Inoculated plants produced significantly more shoot and root biomass (FIG. 19). Non-inoculated plants leaves were wilted at the end of the study while inoculated plants remained healthy.

Figure 20:
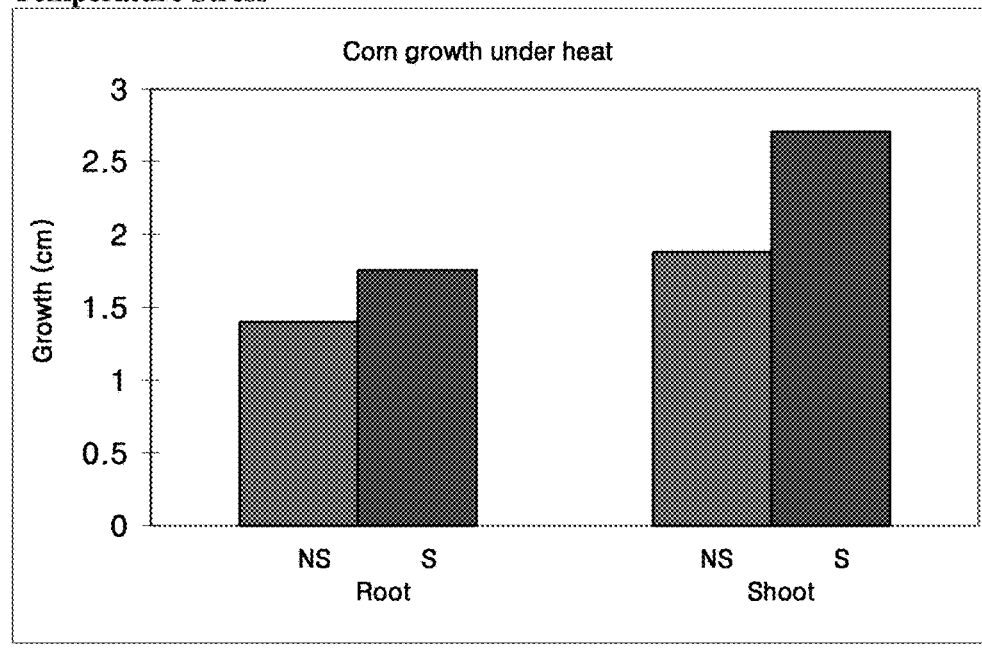
FIG. 20 is a bar graph depicting the growth of nonsymbiotic (NS) or ThLm1 symbiotic (S) corn plants exposed to high temperatures. Growth of symbiotic (right bars in each pair) and nonsymbiotic (left bars in each pair) corn plants was measured after two weeks of exposure to high temperatures (45-50° C.).

Corn plants inoculated or not inoculated with ThLm1 were assessed for growth under high temperature stress. Growth was measured after two weeks of exposure to high temperatures (45-50° C.). ThLm1 inoculated plants grew more than non-inoculated plants under heat stress (FIG. 20). Non-inoculated plants were wilted while the inoculated plants remained healthy.

Figure 21:
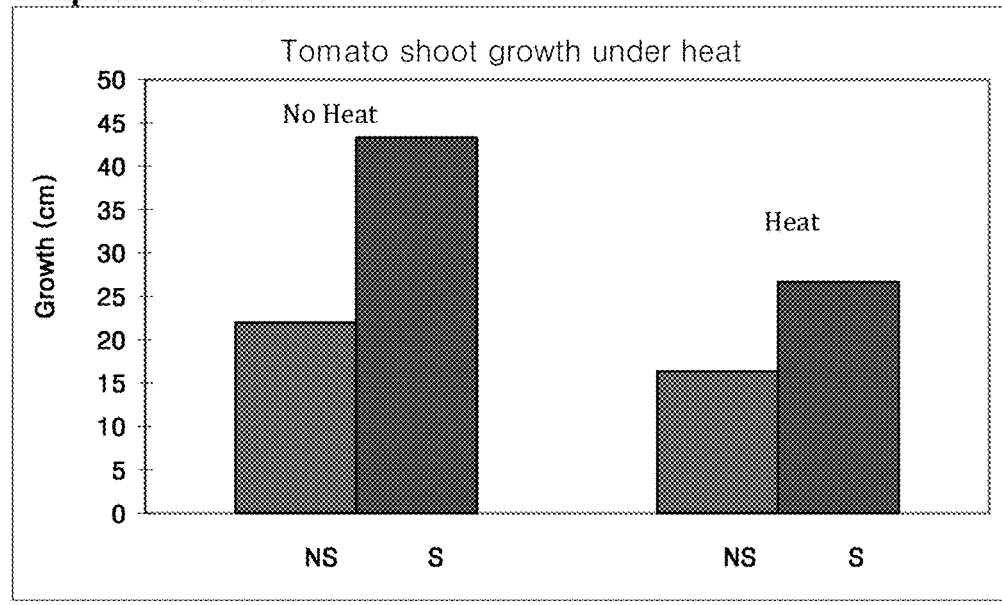
FIG. 21 is a bar graph depicting the growth of nonsymbiotic (NS) or ThLm1 symbiotic (S) tomato plants exposed to high temperatures. Growth of symbiotic (right bars in each pair) and nonsymbiotic (left bars in each pair) corn plants was measured after two weeks of exposure to high temperatures (45-50° C., right pair) or normal temperatures (25-30° C., left pair).

Tomato plants inoculated or not inoculated with ThLm1 were assessed for growth under high temperature stress. Growth was measured after two weeks of exposure to high temperatures (45-50° C.). ThLm1 inoculated plants grew more than non-inoculated plants under heat stress (FIG. 21). Non-inoculated plants were wilted while the inoculated plants remained healthy.

Figure 22:
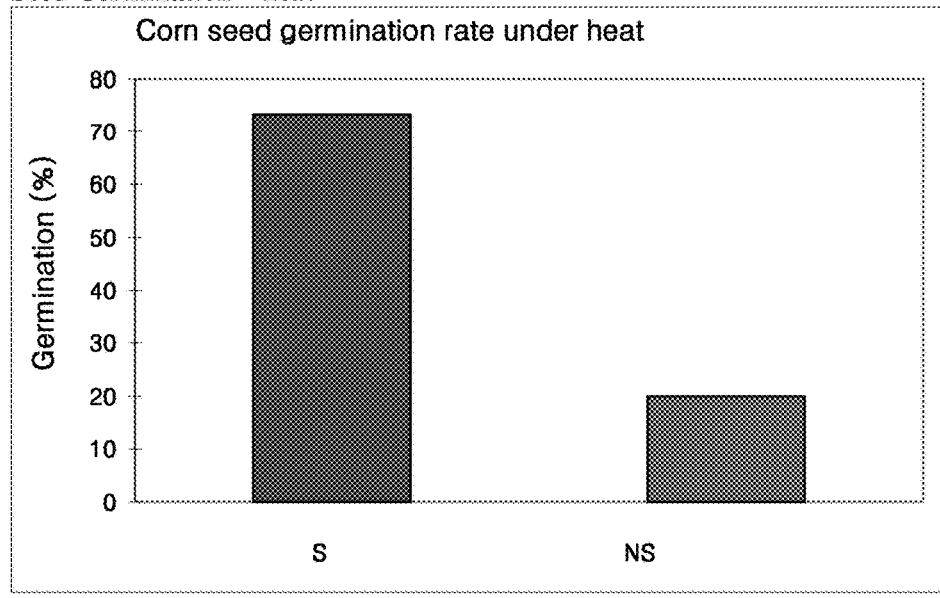
FIG. 22 is a graph of the percent germination of corn seeds treated with ThLm1 (S) or not treated with ThLm1 (NS) under high heat (50-55° C.).

Corn seeds treated or not treated with ThLm1 were assessed for germination under high temperature stress (50-55° C.). Seeds (N=15) treated with ThLm1 germinated significantly better than untreated control seeds (FIG. 22).

Figure 23:
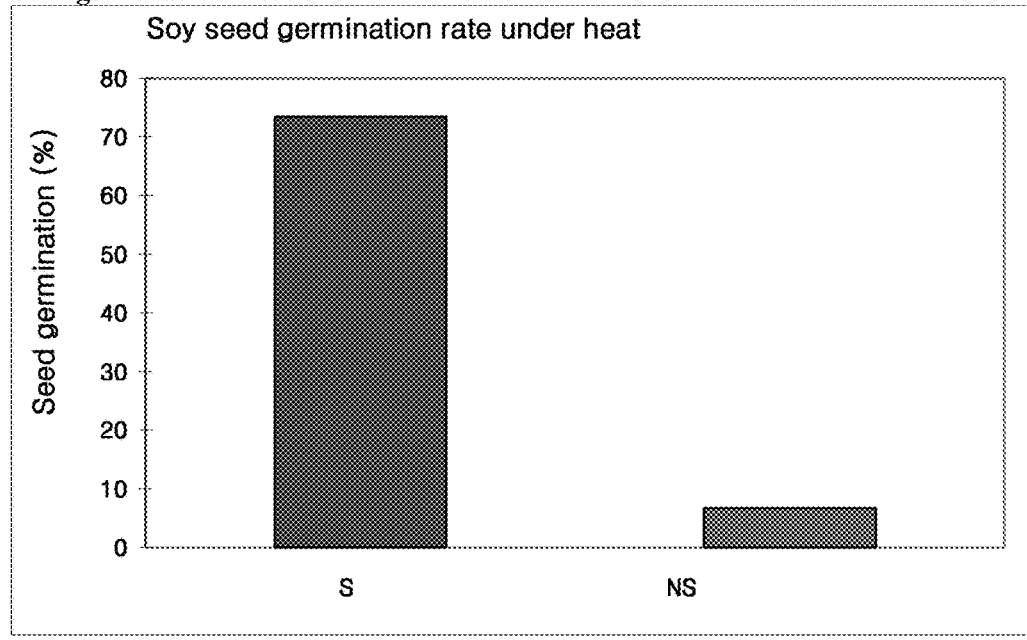
FIG. 23 is a graph of the percent germination of soybean seeds treated with ThLm1 (S) or not treated with ThLm1 (NS) under high heat (50-55° C.).

Soybean seeds treated or not treated with ThLm1 were assessed for germination under high temperature stress (50-55° C.). Seeds (N=15) treated with ThLm1 germinated significantly better than untreated control seeds (FIG. 23).

Figure 24:
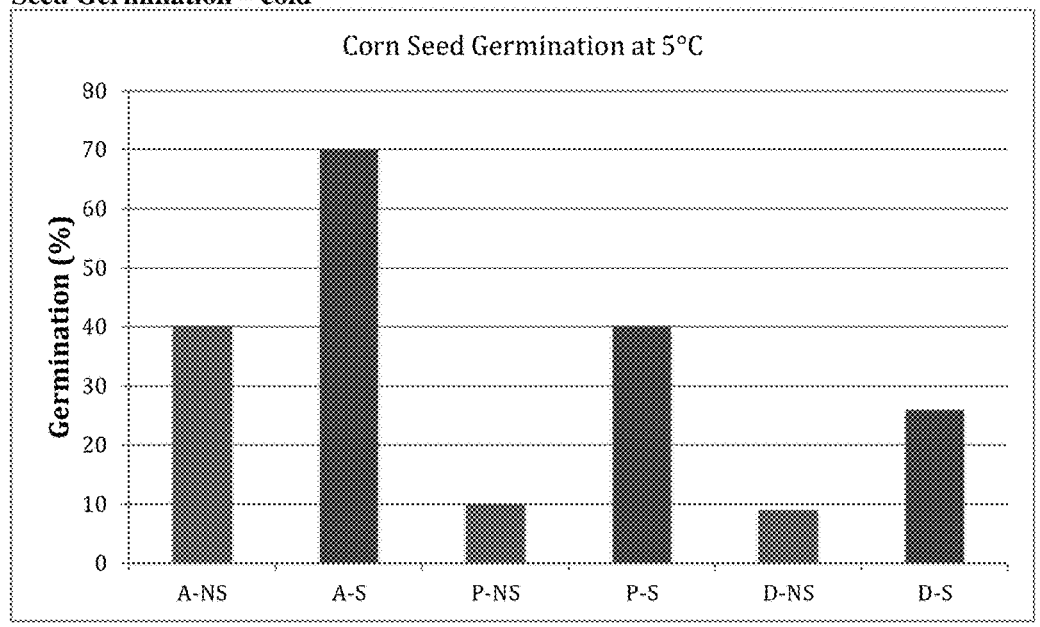
FIG. 24 is a graph of the percent germination of corn seeds treated with ThLm1 (S) or not treated with ThLm1 (NS) exposed to a cold temperature (5° C.) for 144 hours. Three corn varieties were tested (A, P & D).

Corn seeds treated or not treated with ThLm1 were assessed for germination under low temperature stress. Corn seeds were exposed to a cold temperature (5° C.) for 144 hours. Seeds (N=30) treated with ThLm1 germinated significantly better than untreated control seeds (FIG. 24).

Figure 25:
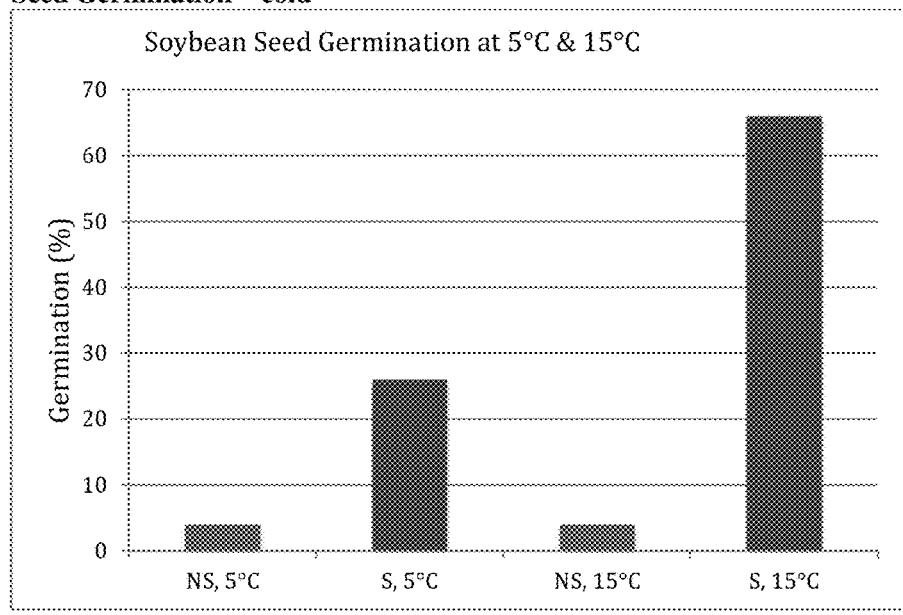
FIG. 25 is a graph of the percent germination of soybean seeds treated with ThLm1 (S) or not treated with ThLm1 (NS) exposed to a cold temperature (5° C. or 15° C.) for 72 hours.
Figure 26:
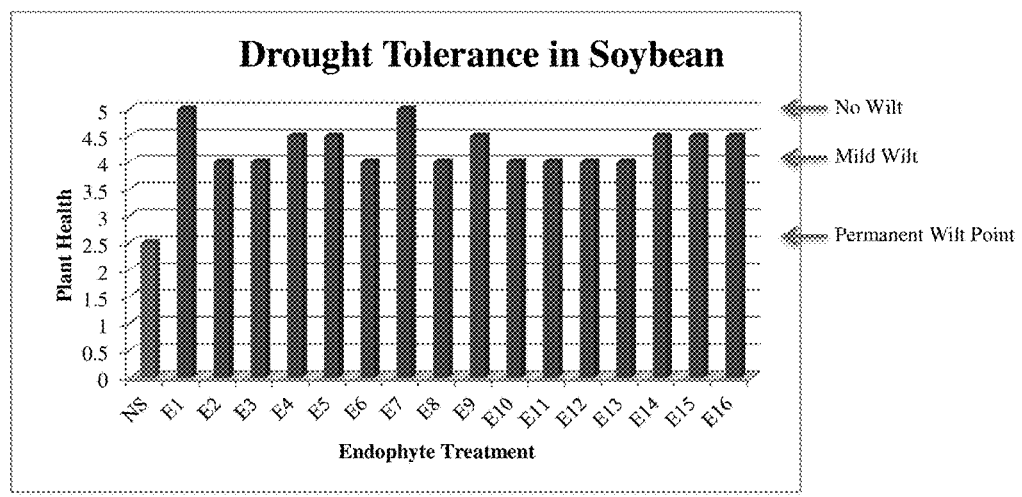
FIG. 26 is a graph showing drought stress tolerance conferred to soybean plants by 16 geographically diverse isolates of *T. harzianum*. NS (Nonsymbiotic) represents control plants without an endophyte and each bar represents four replicates of 9 plants (n=36). Plants were exposed to 9 days of drought stress (complete lack of watering) and standard deviations were less than 5%. No wilt=plants with full turgor no different from plants grown without plant stress; Mild wilt=plants with full turgor but mild leaf curling at tips; Permanent wilt point=severe wilt that plants do not recover from when re-watered.
Figure 27:
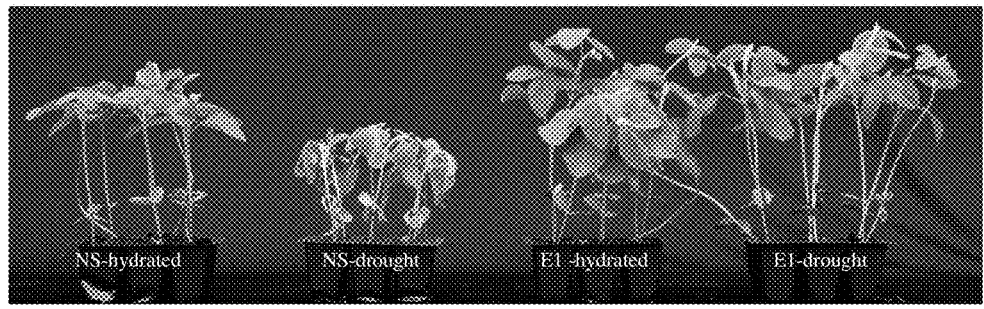
FIG. 27 is a representative image of drought tolerance conferred to soybeans by *T. harzianum* isolates. Plants were exposed to 6 days of drought conditions and all NS plants wilted while E1 colonized plants retained all turgor. The E1 colonized plants also continued to grow during the drought stress as seen by plant sizes.
Figure 28:
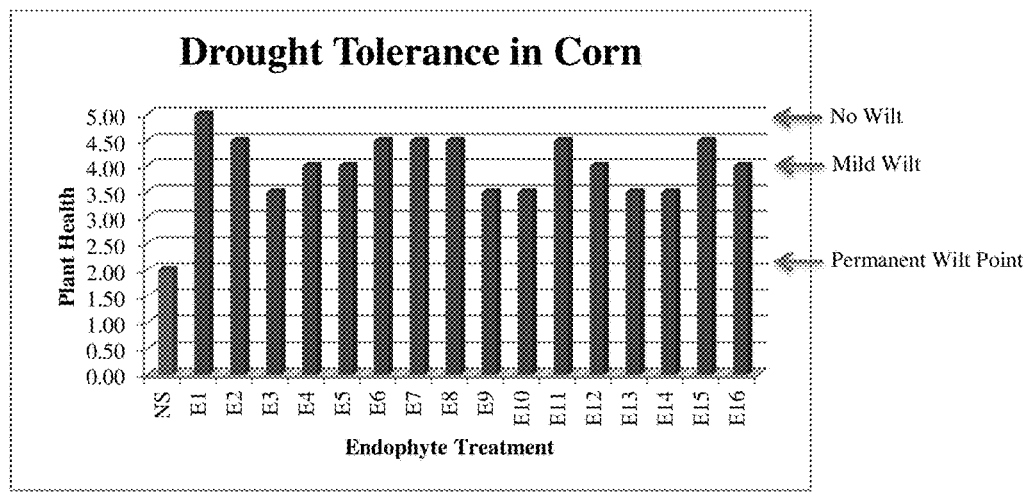
FIG. 28 is a graph showing drought stress tolerance conferred to corn plants by 16 geographically diverse isolates of *T. harzianum*. NS (Nonsymbiotic) represents control plants without an endophyte and each bar represents four replicates of 9 plants (n=36). Plants were exposed to 9 days of drought stress (complete lack of watering) and standard deviations were less than 5%. No wilt=plants with full turgor no different from plants grown without plant stress; Mild wilt=plants with full turgor but mild leaf curling at tips; Permanent wilt point=severe wilt that plants do not recover from when re-watered.
Figure 29:
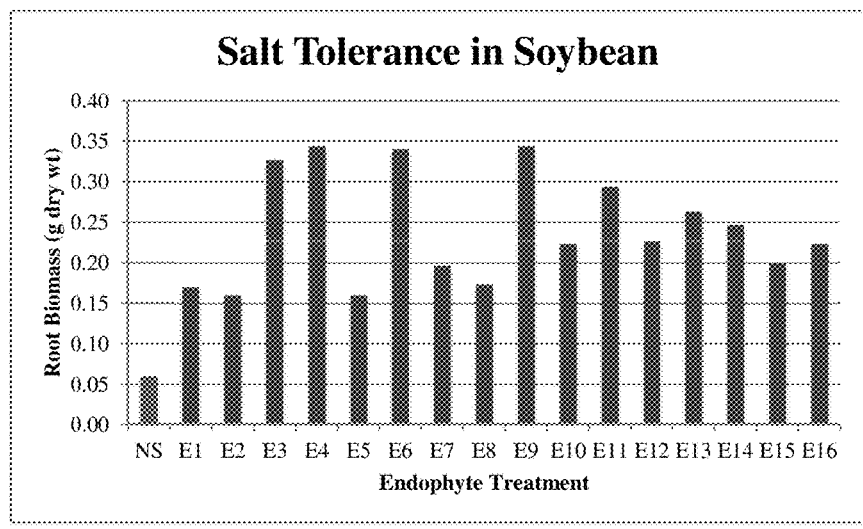
FIG. 29 is a graph showing salt stress tolerance conferred to soybean plants by 16 geographically diverse isolates of *T. harzianum*. NS (Nonsymbiotic) represents control plants without an endophyte and each bar represents four replicates of 9 plants (n=36). Plants were exposed to 14 days of salt stress (300 mM NaCl) with standard deviations<10%. All endophytes significantly increased plant root biomass compared to nonsymbiotic control plants. All symbiotic plants were healthy while NS plants were chlorotic and wilting.
Figure 30:
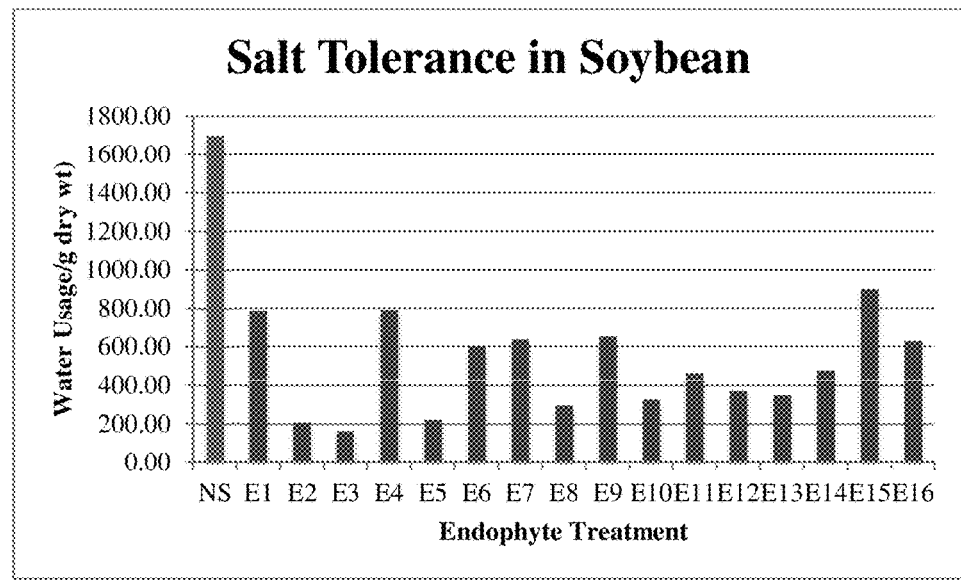
FIG. 30 is a graph showing salt stress tolerance conferred to soybean plants by 16 geographically diverse isolates of *T. harzianum*. NS (Nonsymbiotic) represents control plants without an endophyte and each bar represents four replicates of 9 plants (n=36). Plants were exposed to 14 days of salt stress (300 mM NaCl) with standard deviations<10%. All endophytes decreased water usage by more than 100% compared to nonsymbiotic control plants. All symbiotic plants were healthy while NS plants were chlorotic and wilting.
Figure 31:
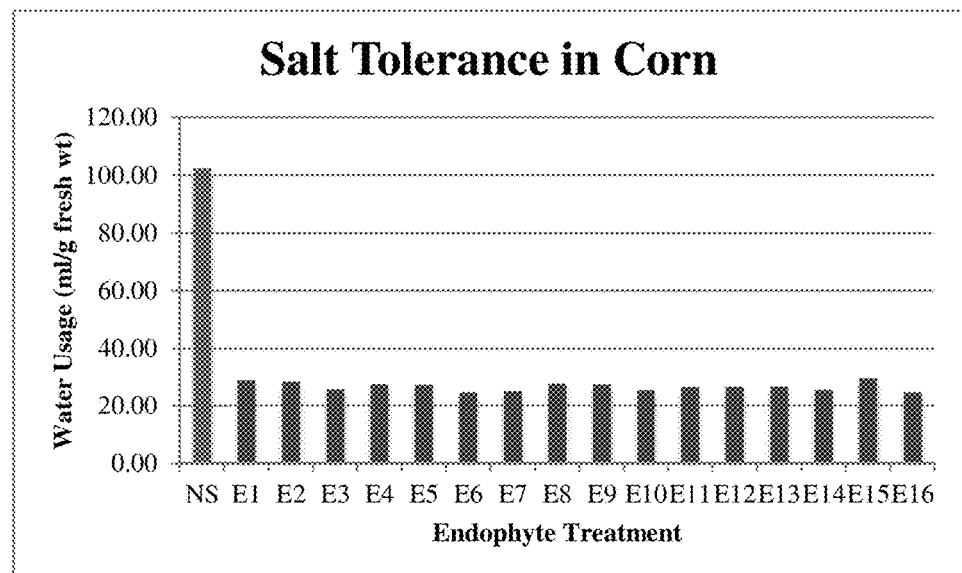
FIG. 31 is a graph showing salt stress tolerance conferred to corn plants by 16 geographically diverse isolates of *T. harzianum*. NS (Nonsymbiotic) represents control plants without an endophyte and each bar represents four replicates of 9 plants (n=36). Plants were exposed to 14 days of salt stress (300 mM NaCl) with standard deviations<10%. All endophytes decreased water usage by more than 300% compared to nonsymbiotic control plants. All symbiotic plants were healthy while NS plants were chlorotic and wilting.
Figure 32:
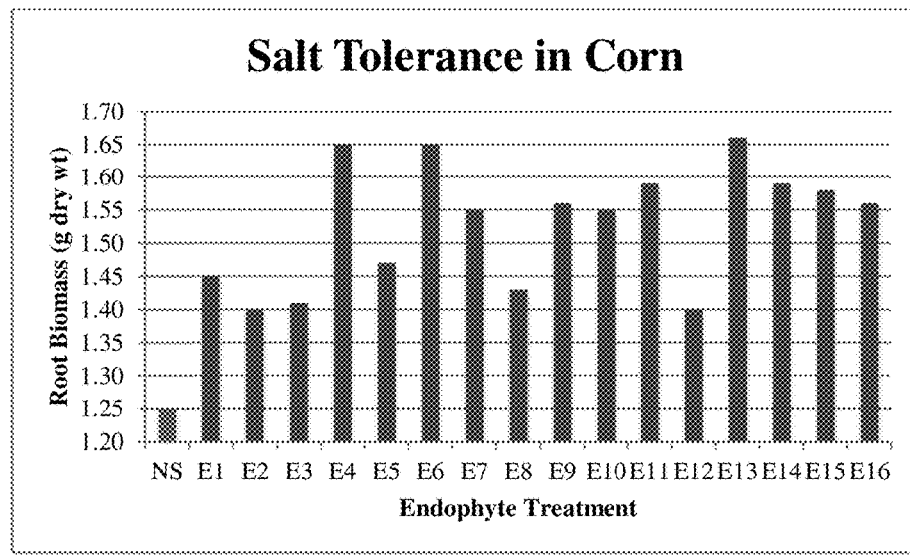
FIG. 32 is a graph showing salt stress tolerance conferred to corn plants by 16 geographically diverse isolates of *T. harzianum*. NS (Nonsymbiotic) represents control plants without an endophyte and each bar represents four replicates of 9 plants (n=36). Plants were exposed to 14 days of salt stress (300 mM NaCl) with standard deviations<10%. All endophytes increased plant root biomass by 12-32% compared to nonsymbiotic control plants. All symbiotic plants were healthy while NS plants were chlorotic and wilting.
Figure 33:
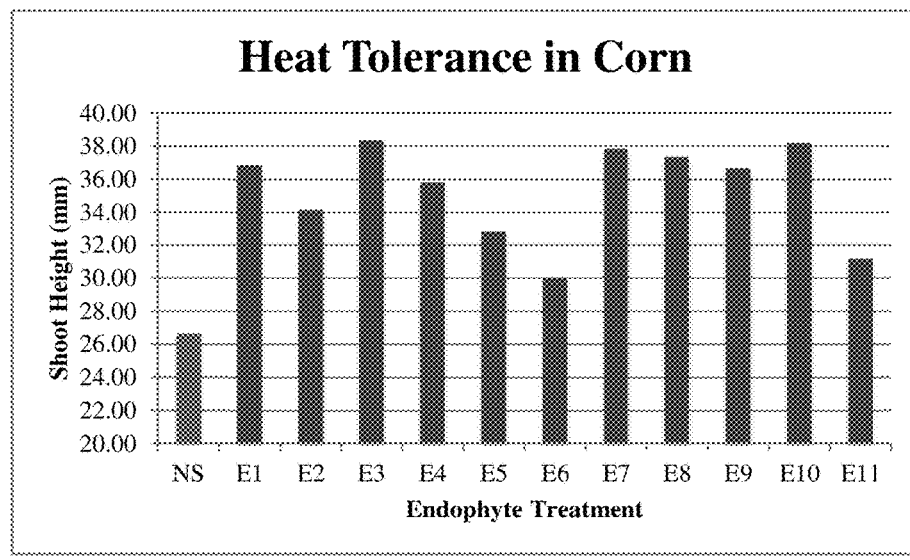
FIG. 33 is a graph showing heat tolerance conferred to corn plants by 11 geographically diverse isolates of *T. harzianum*. NS (Nonsymbiotic) represents control plants without an endophyte and each bar represents four replicates of 9 plants (n=36). Plants were exposed to 10 days of 45° C. root temperatures with standard deviations<10%. All endophytes increased plant shoot height by 15-46% compared to nonsymbiotic control plants. All symbiotic plants were healthy while NS plants were chlorotic and wilting.
Figure 34:
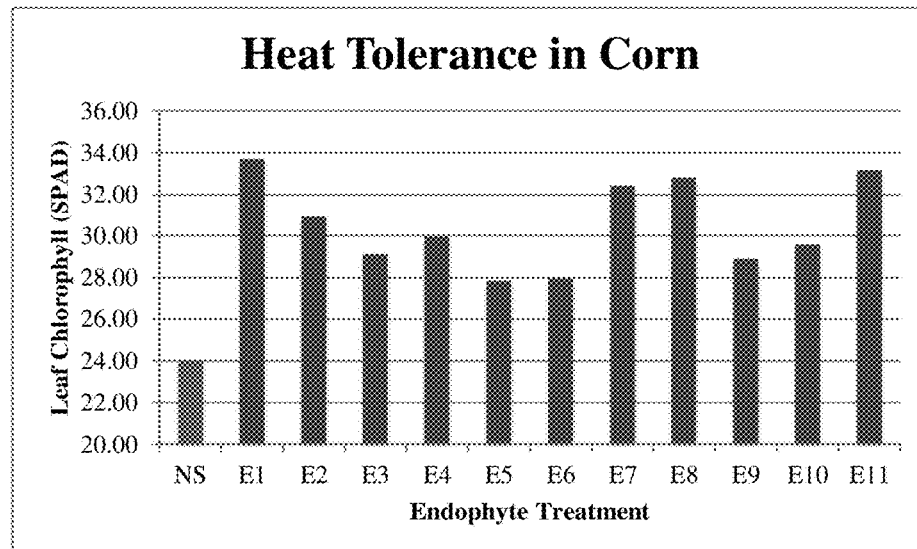
FIG. 34 is a graph showing heat tolerance conferred to corn plants by 11 geographically diverse isolates of *T. harzianum*. NS (Nonsymbiotic) represents control plants without an endophyte and each bar represents four replicates of 9 plants (n=36). Plants were exposed to 10 days of 45° C. root temperatures with standard deviations<10%. All endophytes increased plant leaf chlorophyll levels by 16-37% compared to nonsymbiotic control plants. All symbiotic plants were healthy while NS plants were chlorotic and wilting.
Figure 35:
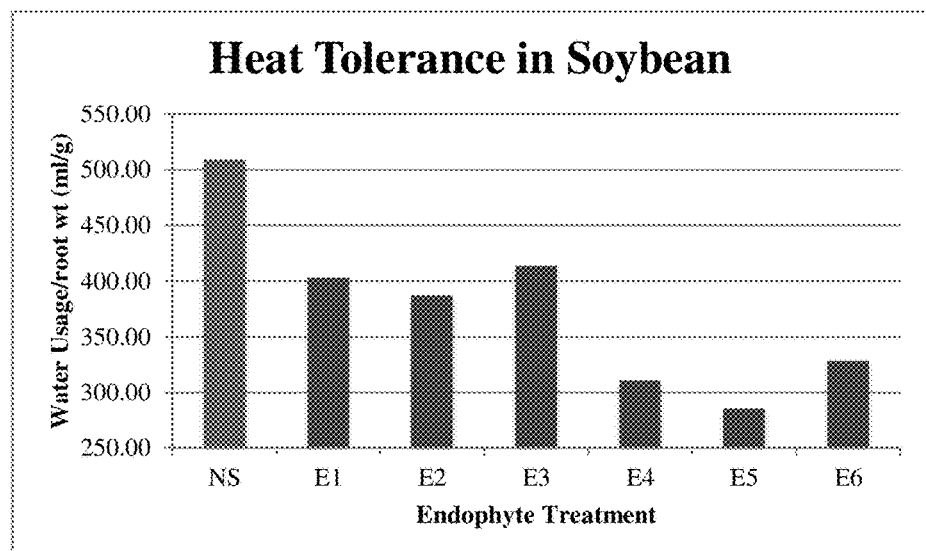
FIG. 35 is a graph showing heat tolerance conferred to soybean plants by 6 geographically diverse isolates of *T. harzianum*. NS (Nonsymbiotic) represents control plants without an endophyte and each bar represents four replicates of 9 plants (n=36). Plants were exposed to 10 days of 45° C. root temperatures with standard deviations<10%. All endophytes decreased plant water use by 26-77% compared to nonsymbiotic control plants. All symbiotic plants were healthy while NS plants were chlorotic and wilting.
Figure 36:
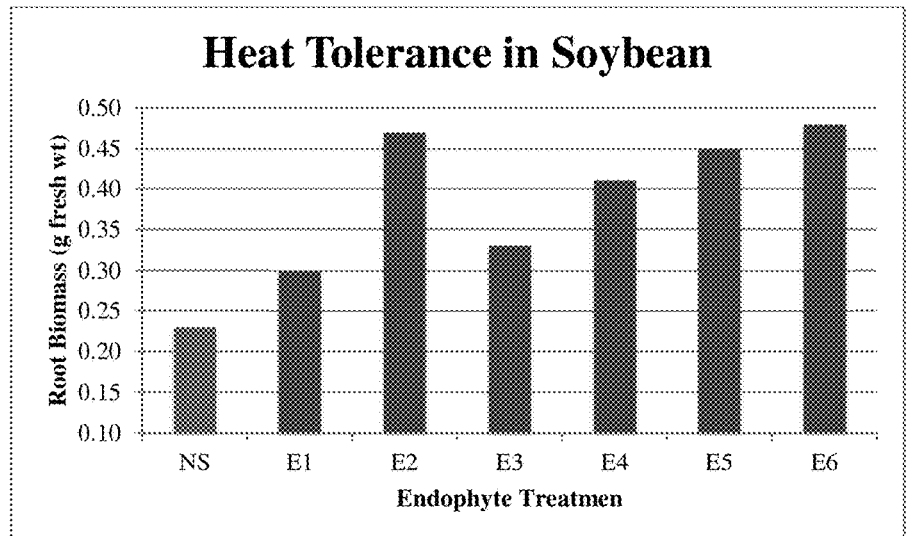
FIG. 36 is a graph showing heat tolerance conferred to soybean plants by 6 geographically diverse isolates of *T. harzianum*. NS (Nonsymbiotic) represents control plants without an endophyte and each bar represents four replicates of 9 plants (n=36). Plants were exposed to 10 days of 45° C. root temperatures with standard deviations<10%. All endophytes increased plant root biomass by 30-100% compared to nonsymbiotic control plants. All symbiotic plants were healthy while NS plants were chlorotic and wilting.
Figure 37:
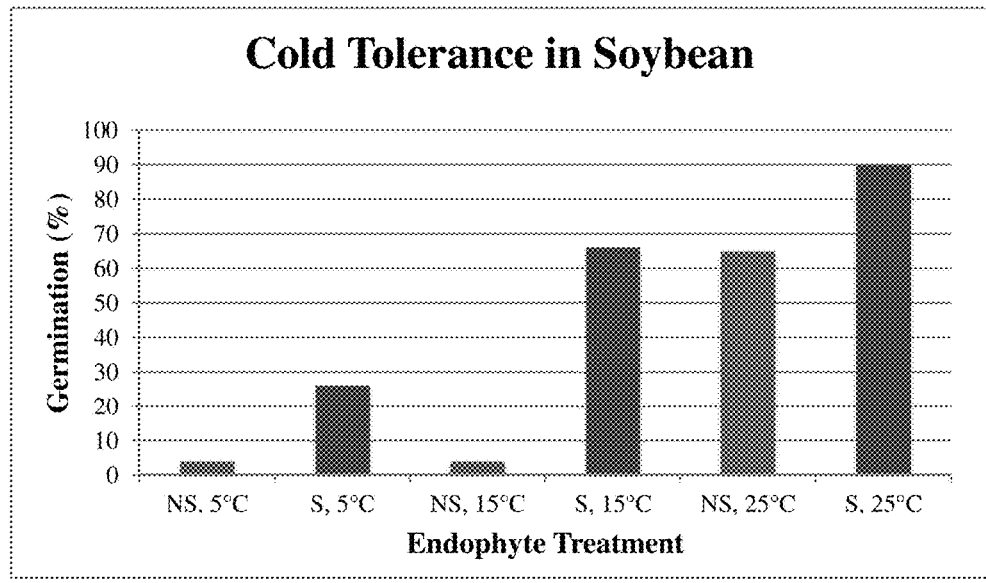
FIG. 37 is a graph showing cold tolerance conferred to soybean plants by an isolate (ThLm1) of *T. harzianum*. NS (Nonsymbiotic) represents control plants without an endophyte and each bar represents three replicates of 9 seeds (n=27, standard deviations<10%). Seeds were inoculated and placed at either 5° C., 15° and 25° C. for 72 hours to assess germination. The endophyte conferred cold tolerance and increased seed germination at all temperatures compared to nonsymbiotic control plants.
Figure 38:
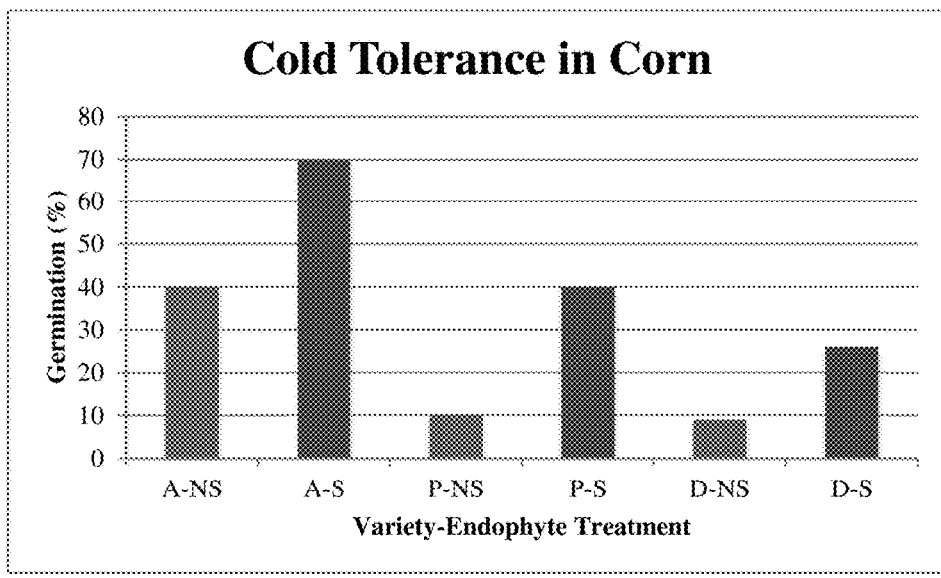
FIG. 38 is a graph showing cold tolerance conferred to corn plants by an isolate (ThLm1) of *T. harzianum*. NS (Nonsymbiotic) represents control plants without an endophyte and each bar represents three replicates of 9 seeds (n=27, standard deviations<10%). Seeds of three corn varieties (A,P,D) were inoculated and placed at 15° Ç 96 hours to assess germination. The endophyte conferred cold tolerance and significantly increased seed germination compared to nonsymbiotic control plants.

Soybean seeds treated or not treated with ThLm1 were assessed for germination under low temperature stress. Soybean seeds were exposed to a cold temperature (5° C. or 15° C.) for 72 hours. Seeds (N=30) treated with ThLm1 germinated significantly better than untreated control seeds (FIG. 25).

Together, these data suggest that inoculation with ThLm1 improved plant health and growth, including root and shoot mass, yield, and germination, under stress conditions such as drought, salt, high temperature, and low temperature.

Figure 39:
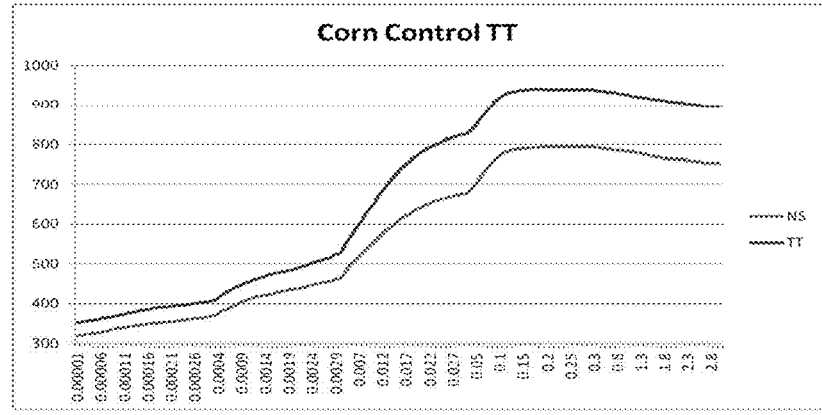
FIGS. 39A-39C present a series of graphs showing the photosynthetic efficiency ($Q_{max}$, Y-axes) measured over time in nonsymbiotic (NS) and symbiotic (TT=ThLM1) corn seedlings two weeks post germination. Plants were grown without stress (FIG. 39A), or in the presence of drought stress (FIG. 39B) or heat stress (FIG. 39C). In all cases, quantum efficiency was significantly higher in symbiotic plants.
Figure 39:
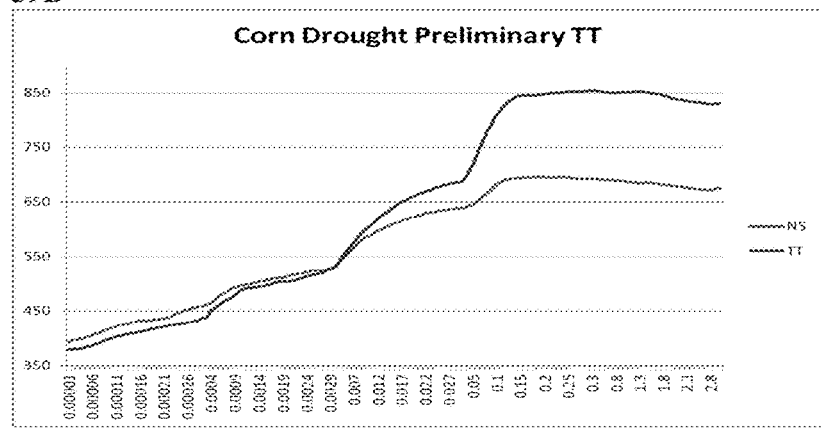
Figure 39:
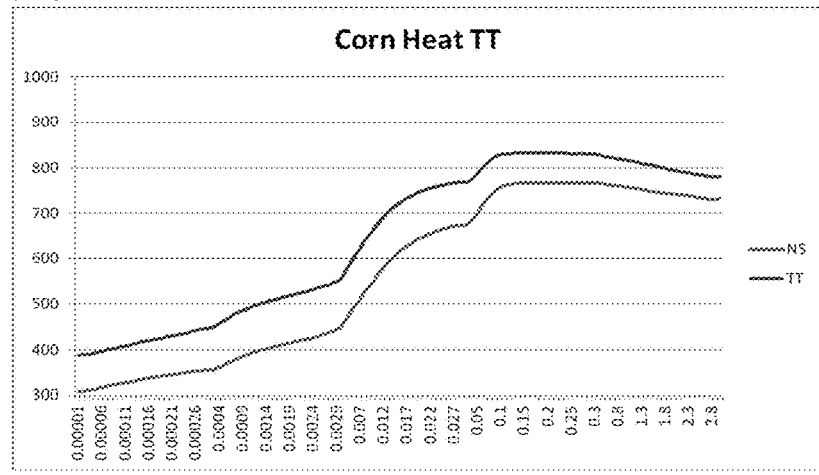
Figure 40:
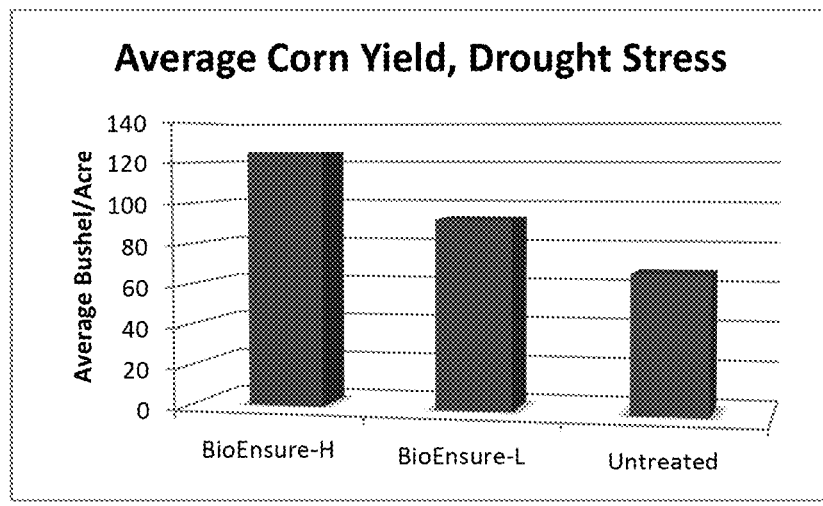
FIG. 40 is a bar graph showing the average corn yield following drought stress at one location in Michigan, USA. The site was subjected to randomized design with 25 plots (20 feet×20 feet each). Four corn varieties were tested with 2 BioEnsure® (formulated ThLm1) treatments (L=low number of spores/seed & H=high number of spores/seed) and there were 10 replicates/treatment with N=30/treatment). Seeds were inoculated with powder formulations of BioEnsure® and were planted within 2 hours. (All other field studies involved liquid formulations.) Treatment with BioEnsure® resulted in 30-85% increase in corn yield relative to plants that did not receive the treatment.
Figure 41:
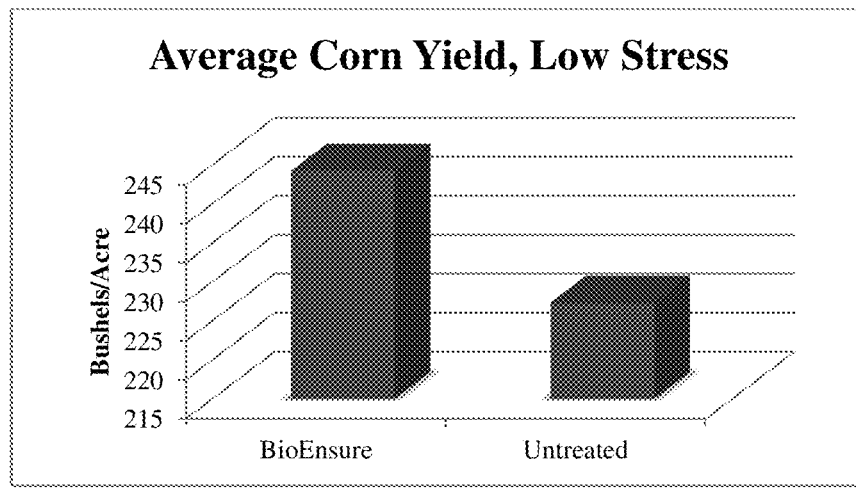
FIG. 41 is a bar graph showing the average corn yield with low stress at sites established by independent cooperators in several ecozones in Michigan and Indiana, USA. The sites were subjected to randomized design with a total of 215 plots. Overall 84% of plots treated with BioEnsure® (formulated ThLm1) had an increase in corn yield with the average being a 6.5% increase and a range of 3-20% increase. The increase in bushels/acre ranged from 5-38.
Figure 42:
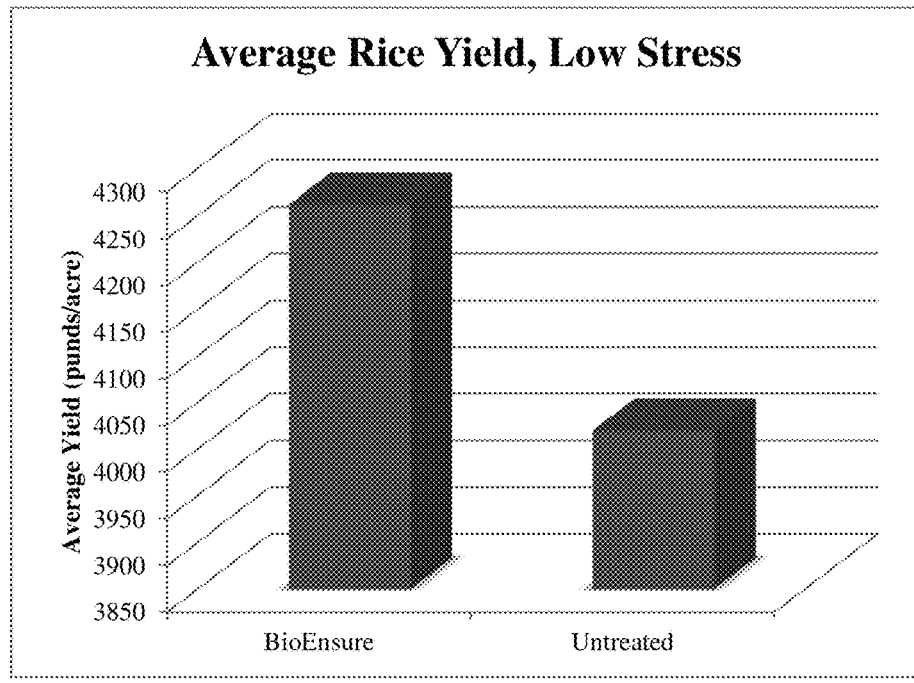
FIG. 42 is a bar graph showing the average rice yield with low stress in plots established in two soil types in Texas, USA. The sites were subjected to randomized design with a total of 105 plots (20 feet×20 feet each). Three rice varieties were tested with 2 BioEnsure® (formulated ThLm1) treatments, and there were 4 replicates/treatment drill seeded at 80 lb/acre. BioEnsure® induced yield increases ranged from 191-657 lbs/acre with a field average increase of 6% and a range from 2.1-18.2%.
Figure 43:
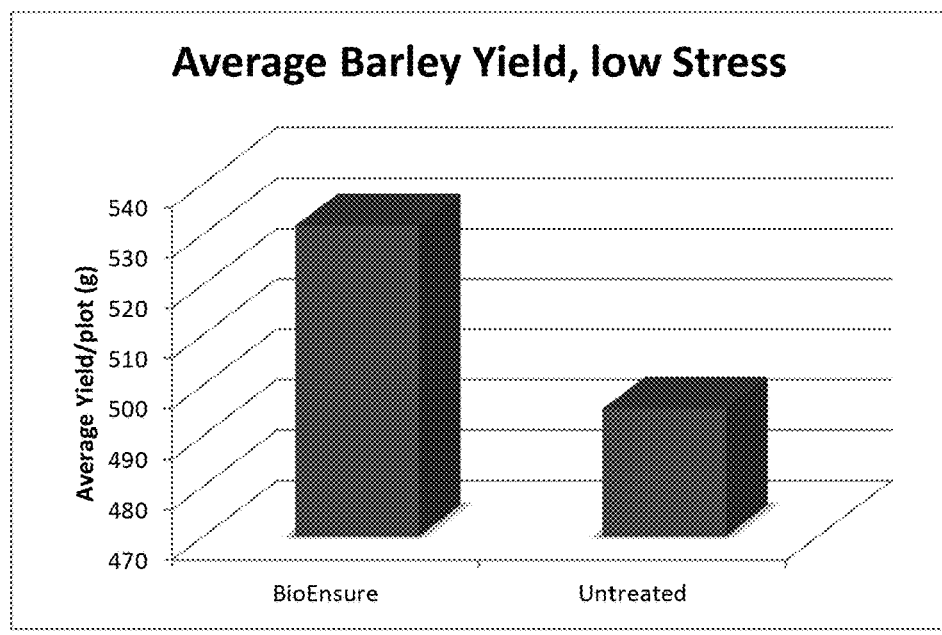
FIG. 43 is a bar graph showing the average barley yield in low stress. One barley variety was planted in 18 randomized plots (20 feet×20 feet each). BioEnsure® (formulated ThLm1) treatment increased barley yield by 7%.
Figure 44:
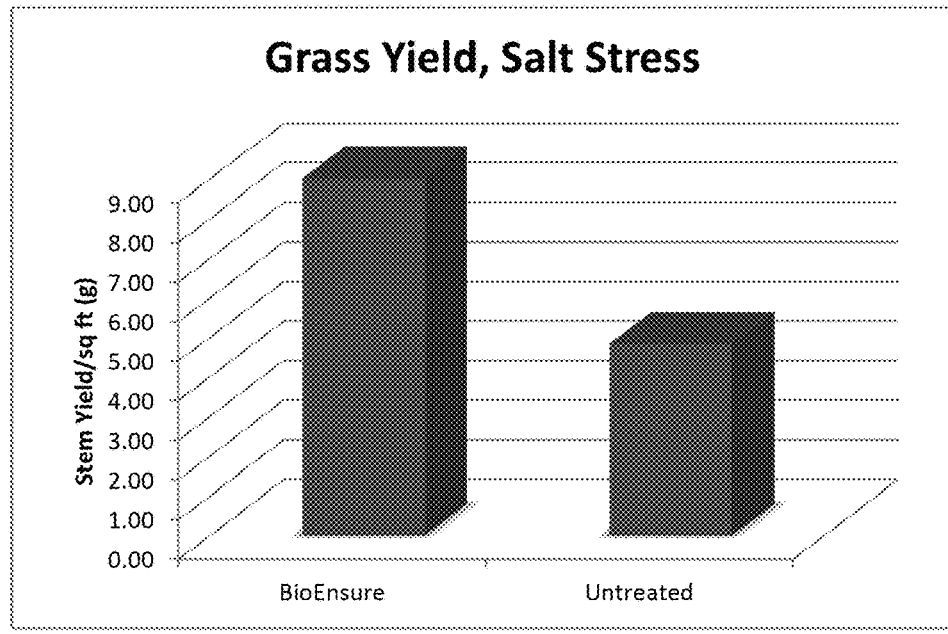
FIG. 44 is a bar graph showing the grass yield in salt stress. A total of 18 plots of grass were assessed in the presence of constant salt stress of 30-80 mM. The BioEnsure® (formulated ThLm1)-treated plants had 86% more biomass than plants that did not receive the treatment (untreated).

ThLm1 Increases the Photosynthetic Efficiency in the Presence and Absence of Stress The photosynthetic efficiency (Qmax) is the fraction of light energy converted into chemical energy during photosynthesis. Several studies with ThLm1 in both the presence or absence of stress revealed that treatment of plants with ThLm1 resulted in an increase in Qmax in both monocots and eudicots, as shown for example in FIG. 39A-39C for corn.

ThLm1 Increases Crop Yields in the Presence and Absence of Stress

Two years of field tests were performed in 8 states with BioEnsure® (formulated ThLm1) inoculated and non-inoculated seeds of corn, rice, grains, and grass (FIGS. 40-44). Field testing was performed under conditions of high drought and salt stress, or very low stress levels (normal growing season). BioEnsure® increased crop yields under all conditions although greater yield increases were observed under high levels of stress. Yield increases occurred irrespective of soil type and climate zone.

SUMMARY

Taken together, the data show that inoculation with ThLm1 increased seed germination rates and plant growth, conferred tolerance to various stresses (salt, temperature, drought, nutrients), enhanced general robustness and health (such as an increase in % chlorophyll), and increased yields.

Example 3. Effects of *T. harzianum* Isolates on Increasing Stress Tolerance, Increasing Germination and Excluding Other Fungi Strains of *T. harzianum* isolated from a diversity of geographic locations (the origin of 16 of the strains are noted in Table 4) were used to assess benefits of *T. harzianum* strains in addition to ThLm1, using methods as described in the examples above.

TABLE 4

Geographic Diversity of *T. harzianum* strains used

| Strain | Origin |
| --- | --- |
| E1 | USA, WA |
| E2 | USA, NY |
| E3 | USA, OH |
| E4 | USA, FL |
| E5 | USA, TX |
| E6 | USA, GA |
| E7 | USA, AL |
| E8 | Columbia |
| E9 | India |
| E10 | France |
| E11 | Belgium |
| E12 | Tokyo |
| E13 | United Kingdom |
| E14 | French Guiana |
| E15 | Spain |
| E16 | Canada |

The results are depicted in FIGS. 26-38, 45-48, 50 and 51 for drought stress tolerance, salt stress tolerance, temperature tolerance (heat and cold tolerance), and low nutrient tolerance conferred to plants by geographically diverse isolates of *T. harzianum*. Not all of the geographically diverse isolates of *T. harzianum* were used in each experiment or condition, but the results clearly support the use of *T. harzianum* generally for increasing tolerance to a variety of stresses.

Figure 45:
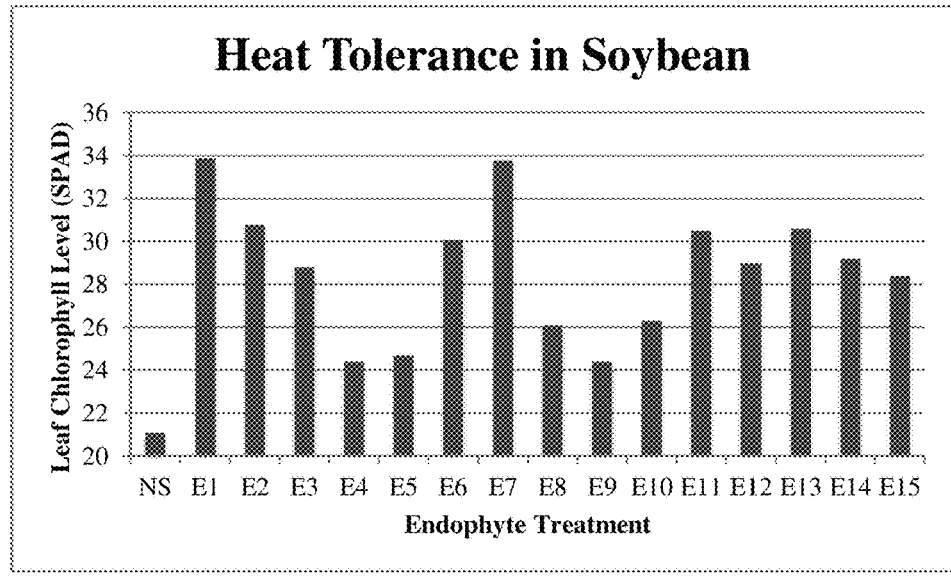
FIG. 45 is a bar graph showing heat tolerance conferred to soybean plants by 15 geographically diverse isolates of *T. harzianum*. NS (Nonsymbiotic) represents control plants without an endophyte and each bar represents four replicates of 9 plants (n=36). Plant roots were exposed to 10 days of 45° C. with standard deviations<10%. All endophytes increased plant leaf chlorophyll levels by 16-37% compared to nonsymbiotic control plants. All symbiotic plants were healthy while NS plants were chlorotic and wilting.
Figure 46:
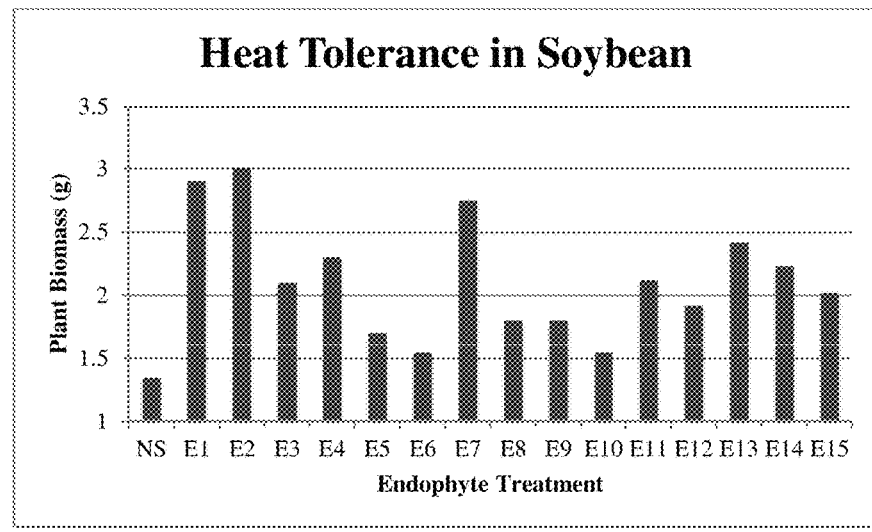
FIG. 46 is a bar graph showing heat tolerance conferred to soybean plants by 15 geographically diverse isolates of *T. harzianum*. NS (Nonsymbiotic) represents control plants without an endophyte and each bar represents four replicates of 9 plants (n=36). Plant roots were exposed to 10 days of 45° C. with standard deviations<10%. All endophytes increased plant biomass compared to nonsymbiotic control plants. All symbiotic plants were healthy while NS plants were chlorotic and wilting.
Figure 47:
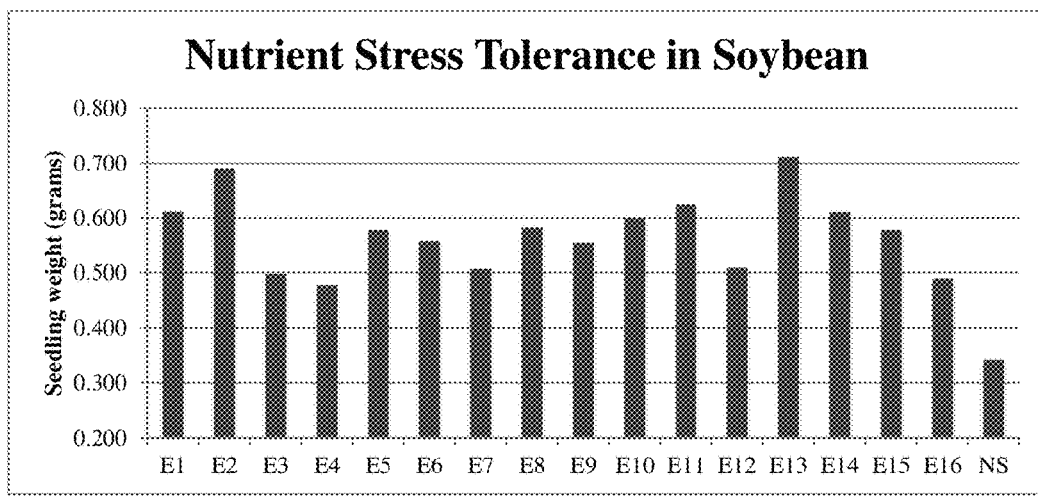
FIG. 47 is a bar graph showing nutrient tolerance conferred to soybean plants by 16 geographically diverse isolates of *T. harzianum*. One-week old soybean plants were given an initial watering with nitrogen, phosphorus, potassium (NPK), after which plants were exposed every 2 days to no NPK stress (watered with full strength NPK) or high NPK stress (watered with ¼ strength NPK) for the duration of the experiments (approximately 90 days). Plants were then assessed for biomass (roots and shoots) and data are shown for the high NPK stress plants. NS (nonsymbiotic) represents control plants without an endophyte.

Soybean plants inoculated or not inoculated with geographically diverse isolates of *T. harzianum* were assessed for growth under high temperature stress. Growth was measured after two weeks of exposure to high temperatures (45-50° C.). Plants inoculated with geographically diverse isolates of *T. harzianum* had increased leaf chlorophyll levels and higher plant biomass more than non-inoculated plants under heat stress (FIGS. 45 and 46).

Figure 48:
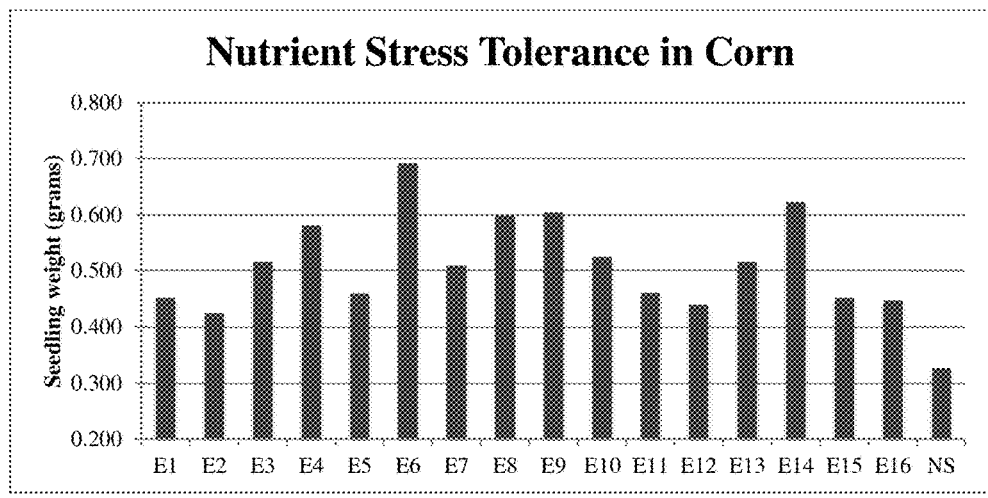
FIG. 48 is a bar graph showing nutrient tolerance conferred to corn plants by 16 geographically diverse isolates of *T. harzianum*. One-week old corn plants were given an initial watering with nitrogen, phosphorus, potassium (NPK), after which plants were exposed every 2 days to no NPK stress (watered with full strength NPK) or high NPK stress (watered with ¼ strength NPK) for the duration of the experiments (approximately 90 days). Plants were then assessed for biomass (roots and shoots) and data are shown for the high NPK stress plants. NS (nonsymbiotic) represents control plants without an endophyte.

Soybean or corn plants inoculated or not inoculated with geographically diverse isolates of *T. harzianum* were assessed for seedling weight under low nutrient stress. One-week old soybean or corn plants were given an initial watering with nitrogen, phosphorus, potassium (NPK), after which plants were exposed every 2 days to no NPK stress (watered with full strength NPK), low NPK stress (watered with ½ strength NPK), or high NPK stress (watered with ¼ strength NPK) for the duration of the experiments (approximately 90 days). Plants were then assessed for seedling weight. Plants inoculated with geographically diverse isolates of *T. harzianum* had higher seedling weight than non-inoculated plants under low nutrient stress (FIG. 47, soybean; FIG. 48, corn).

Figure 50:
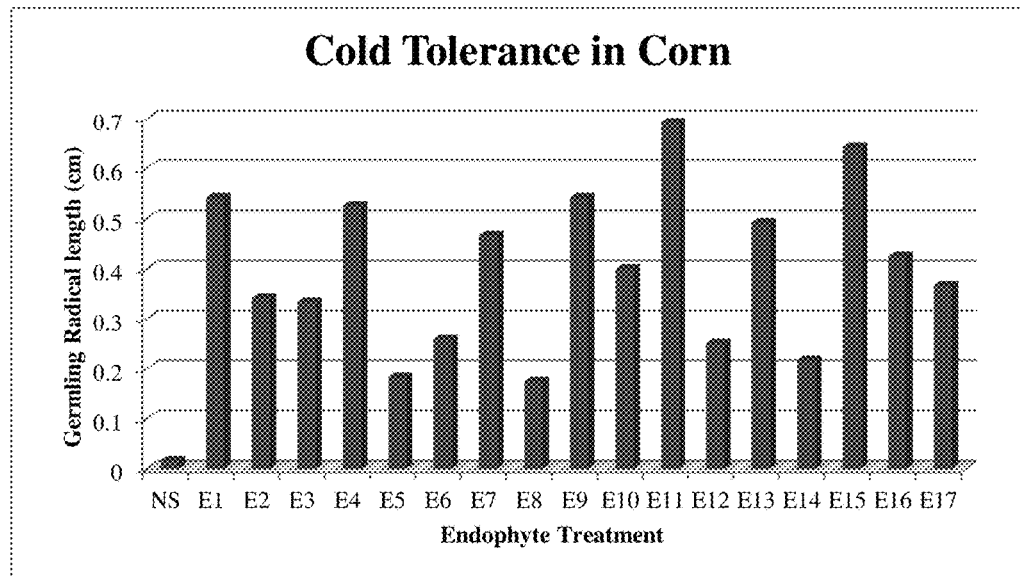
FIG. 50 is a bar graph showing cold tolerance conferred to corn plants by 17 geographically diverse isolates of *T. harzianum*. Cold tolerance is expressed as root radical length from germinated seeds. NS (Nonsymbiotic) represents control plants without an endophyte and each bar represents 30 germlings exposed to 15° C. for 6 days with standard deviations<10%. All endophytes increased germling growth by 10-32× compared to nonsymbiotic control plants. All symbiotic plants were healthy while NS plants were stunted and desiccated.

Further, cold stress tolerance was measured in corn seedlings that were previously inoculated or not inoculated with geographically diverse isolates of *T. harzianum*. The corn seedlings were exposed to cold stress then assessed for germling radical length. Corn inoculated with *T. harzianum* had statistically longer germlings (FIG. 50).

Figure 51:
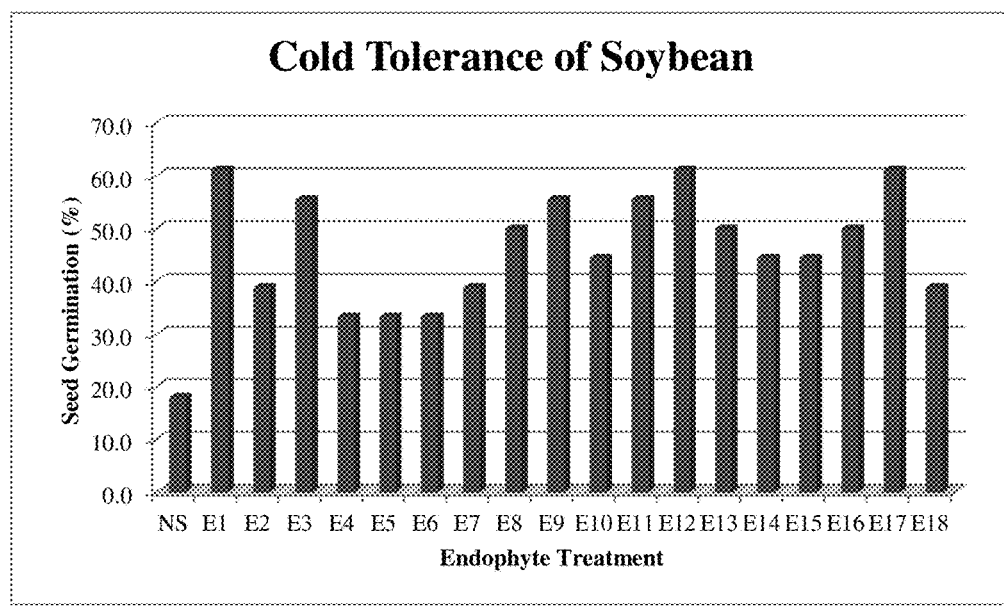
FIG. 51 is a bar graph showing cold tolerance conferred to soybean plants by 18 geographically diverse isolates of *T. harzianum*. Cold tolerance is expressed as seed germination at 15° C. NS (Nonsymbiotic) represents control seeds without an endophyte and each bar represents 18 seeds exposed to 15° C. for 4 days with standard deviations<10%. All endophytes increased seed germination by 85-240% compared to nonsymbiotic control plants.

Cold stress tolerance also was measured in soybean seedlings that were previously inoculated or not inoculated with geographically diverse isolates of *T. harzianum*. The soybean seedlings were exposed to cold stress then assessed for germling radical length. Soybean seedlings inoculated with *T. harzianum* had statistically longer germlings (FIG. 51).

Figure 49:
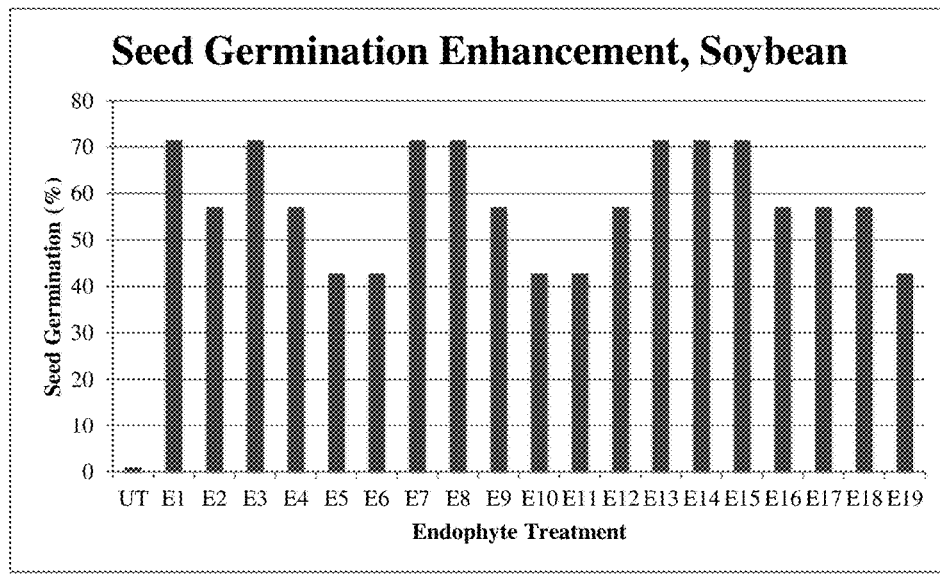
FIG. 49 is a bar graph showing seed germination enhancement conferred to soybean plants by 19 geographically diverse isolates of *T. harzianum*. UT (untreated) represents control seeds without an endophyte, and each bar represents 20 seeds. Data represent the percent enhanced germination above untreated control seeds. All endophytes increased seed germination 40-70× compared to untreated control seeds.

In other experiments, geographically diverse isolates of *T. harzianum* were tested for their effects on germination of seeds, using the methodology described herein, as shown in FIG. 49. Soybean seeds inoculated or not inoculated with geographically diverse isolates of *T. harzianum* were assessed for germination. Soybean seeds inoculated with geographically diverse isolates of *T. harzianum* had a significantly higher % of germination compared to soybean seeds that were untreated (FIG. 49). The results support the use of *T. harzianum* generally for increasing germination of seeds.

In other experiments, the 16 geographically diverse isolates of *T. harzianum* are tested for their effects on establishment of fungi other than *Trichoderma harzianum* in a plant. Seeds or seedlings are inoculated with isolated *T. harzianum* isolates or spores thereof and the seeds or seedlings are grown. The growth of fungi other than the inoculated *T. harzianum* isolates is evaluated. The results support the use of *T. harzianum* generally for reducing establishment of fungi other than *Trichoderma harzianum* in a plant growing from the inoculated seed or seedling.

REFERENCES

Altomare C, Norvell W A, Bjorkman T, Harman G E (1999) Solubilization of phosphates and micronutrients by the plant-growth-promoting and biocontrol fungus *trichoderma harzianum* rifai 1295-22 *Appl Environ Microbiol.* 65: 2926-2933.

Arx JAv (1981). *The genera of fungi sporulating in pure culture*. J. Cramer: Vaduz, 424 pp.

Barnett H L, Hunter B B (1998). *Illustrated genera of imperfect fungi*. American Phytopathology Society St. Paul, 240 pp.

Bacon C W, Hill N S (1996) Symptomless grass endophytes: products of coevolutionary symbioses and their role in the ecological adaptations of grasses. In: Redkin S C, Carris L M, editors. Endophytic fungi in grasses and woody plants. St. Paul: APS Press. pp. 155-178.

Berg, G (2009) Plant-microbe interactions promoting plant growth and health: perspectives for controlled use of microorganisms in agriculture. *Appl Microbiol Biotechnol* 84:11-18.

Clay K, Holah J (1999) Fungal endophyte symbiosis and plant diversity in successional fields. *Science* 285: 1742-1745.

Harman G E, Howell C R, Viterbo A, Chet I, Lorito M (2004) *Trichoderma* species—opportunistic, avirulent plant symbionts. *Nat Rev Microbiol.* 2: 43-56.

Leslie J F, Summerell B A (2005). *The Fusarium Laboratory Manual*. Blackwell Publishing: Ames, 400 pp.

Naseby D C, Pascual J A, Lynch J M (2000) Effect of biocontrol strains of *Trichoderma* on plant growth, *Pythium ultimum* populations, soil microbial communities and soil enzyme activities. *J Appl Microbiol* 88: 161-169.

O'Donnell K, Kistler H C, Tacke B K, Casper H C (2000). Gene genealogies reveal global phylogeographic structure and reproductive isolation among lineages of *Fusarium graminearum*, the fungus causing wheat scab. *Proceedings of the National Academy of Sciences* 97: 7905-7910.

Petrini O (1996) Ecological and physiological aspects of host-specificity in endophytic fungi. In: Redlin S C, Carris L M, editors. Endopytic Fungi in Grasses and Woody Plants. St. Paul: APS Press. pp. 87-100.

Read, D. J.: 1999, 'Mycorrhiza—the state of the art', in A. Varma and B. Hock (eds.), Mycorrhiza, Berlin, Springer-Verlag, pp. 3-34.

Redman R S, Freeman S, Clifton D R, Morrel J, Brown G, Rodriguez R J (1999). Biochemical analysis of plant protection afforded by a nonpathogenic endophytic mutant of *colletotrichum magna*. *Plant Physiology* 119: 795-804.

Redman R S, Dunigan D D, Rodriguez R J (2001). Fungal symbiosis: from mutualism to parasitism, who controls the outcome, host or invader? *New Phytologist* 151: 705-716.

Redman R S, Rossinck M R, Maher S, Andrews Q C, Schneider W L, Rodriguez R J (2002a). Field performance of cucurbit and tomato plants infected with a nonpathogenic mutant of *Colletotrichum magna* (teleomorph: *Glomerella magna*; Jenkins and Winstead). *Symbiosis* 32: 55-70.

Redman R S, Sheehan K B, Stout R G, Rodriguez R J, Henson J M (2002b) Thermotolerance generated by plant/fungal symbiosis. *Science* 298:1581.

Redman R S, Kim Y O, Woodward C J, Greer C, Espino L, Doty S L, Rodriguez R J (2011) Increased fitness of rice plants to abiotic stress via habitat adapted symbiosis: a strategy for mitigating impacts of climate change. *PLoS One* 6:e14823.

Rodriguez R J, Yoder O C (1991). A family of conserved repetitive DNA elements from the fungal plant pathogen *Glomerella cingulata* (*Colletotrichum lindemuthianum*). *Experimental Mycology* 15: 232-242.

Rodriguez R J (1993). Polyphosphates present in DNA preparations from filamentous fungal species of *Colletotrichum* inhibits restriction endonucleases and other enzymes. *Analytical Biochemistry* 209: 1-7.

Rodriguez, R. J. and Redman, R. S.: 1997, 'Fungal lifestyles and ecosystem dynamics: biological aspects of plant pathogens, plant endophytes and saprophytes', Adv. Bot. Res. 24, 169-193.

Rodriguez R, Redman R. (2008) More than 400 million years of evolution and some plants still can't make it on their own: plant stress tolerance via fungal symbiosis. *J Exp Bot.* 59: 1109-1114.

Rodriguez R J, Redman R S, Henson J M. (2004). The role of fungal symbioses in the adaptation of plants to high stress environments. *Mitigation and Adaptation Strategies for Global Change* 9: 261-272.

Rodriguez R. J., Henson J., Van Volkenburgh E., Hoy M., Wright L., Beckwith F., Kim Y., Redman R. S. 2008. Stress Tolerance in Plants via Habitat-Adapted Symbiosis. *ISME-Nature*, 2, 404-416.

Rodriguez R J, Freeman D C, McArthur E D, Kim Y O, Redman R S (2009) Symbiotic regulation of plant growth, development and reproduction. *Commun Integr Biol.* 2: 141-3.

Rodriguez R. J. and Roossinck M. 2012. Viruses, fungi and plants: cross-kingdom communication and mutualism. In, Biocommunication of Fungi, Ed, G. Witzany (ed.), Springer, pg 219-227.

White T J, Bruns T, Lee S, Taylor J (1990). Amplification and direct sequencing of fungal ribosomal RNA genes for phylogenetics. In: Innis M A, Gelfand D H, Sninsky J J and White T J (eds). *PCR Protocols: A Guide to Methods and Applications*. Academic Press, INC.: San Diego. pp 315-322.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for promoting abiotic stress tolerance and/or enhancing plant growth or seed germination under abiotic stress, the method comprising:
   manually or mechanically inoculating a plant or a plant seed with an isolated *Trichoderma harzianum* strain ThLm1 fungus deposited at the Agricultural Research Service Culture Collection under Patent Deposit Designation number NRRL 50846, or a conidium or asexual progeny thereof.

2. The method of claim 1, wherein the abiotic stress tolerance is drought tolerance, salt tolerance, reduced nutrient tolerance, and/or temperature tolerance.

3. The method of claim 1, wherein the enhanced plant growth or seed germination under abiotic stress comprises an increase in size, extent of root development, germination rate of seeds, chlorophyll content/level, photosynthetic efficiency, yield or mass.

4. The method of claim 1, wherein manually or mechanically inoculating the plant comprises colonizing a root and/or stem of the plant with the *Trichoderma harzianum* strain ThLm1 fungus or a conidium or asexual progeny thereof.

5. The method of claim 1, wherein the method further comprises growing the plant or plant seed.

6. The method of claim 5, wherein the plant or plant seed is grown in soil characterized by high salinity, low moisture, and/or low nutrient content, or wherein the plant or plant seed is grown in water characterized by high salinity and/or low nutrient content, or wherein the plant or plant seed is grown or germinated at an average temperature at or above 35 degrees Celsius or at or below 15 degrees Celsius.

7. The method of claim 1, wherein the plant or plant seed is a crop plant or crop plant seed, or an ornamental plant or ornamental plant seed.

8. The method of claim 1, wherein the isolated *Trichoderma harzianum* strain ThLm1 fungus or conidium or asexual progeny thereof is in a composition that is formulated as a liquid or a powder.

9. The method of claim 7, wherein the crop plant or crop plant seed is watermelon, tomato, corn, wheat, soybean, cucurbits, peppers, leafy greens, barley, cotton, beans, peas, tubers, berries, woody plants or rice, or a seed thereof.

10. The method of claim 1, wherein the plant or plant seed is an ornamental, such as Rosaceae, Liliaceae, Azalea, Rhododendron, Poaceae, or Chrysanthemum.

11. The method of claim 1, wherein the plant or plant seed is previously, concurrently and/or subsequently treated with a fungicide and/or insecticide.

\* \* \* \* \*

SEQUENCE LISTING

<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: synthetic polynucleotide

<400> SEQUENCE: 1
tcctccgctt attgatatgc                                              20

<210> SEQ ID NO 2
<211> LENGTH: 22
<212> TYPE: DNA
<213> ORGANISM: artificial sequence
<220> FEATURE:
<223> OTHER INFORMATION: synthetic polynucleotide

<400> SEQUENCE: 2
ggaagtaaaa gtcgtaacaa gg                                           22

<210> SEQ ID NO 3
<211> LENGTH: 20
<212> TYPE: DNA
<213> ORGANISM: artificial sequence
<220> FEATURE:
<223> OTHER INFORMATION: synthetic polynucleotide

<400> SEQUENCE: 3
atgggtaagg aggacaagac                                              20

<210> SEQ ID NO 4
<211> LENGTH: 21
<212> TYPE: DNA
<213> ORGANISM: artificial sequence
<220> FEATURE:
<223> OTHER INFORMATION: synthetic polynucleotide

<400> SEQUENCE: 4
ggaagtacca gtgatcatgt t                                            21

<210> SEQ ID NO 5
<211> LENGTH: 19
<212> TYPE: DNA
<213> ORGANISM: artificial sequence
<220> FEATURE:
<223> OTHER INFORMATION: synthetic polynucleotide

<400> SEQUENCE: 5
gtggggcatt taccccgcc                                               19

<210> SEQ ID NO 6
<211> LENGTH: 19
<212> TYPE: DNA
<213> ORGANISM: artificial sequence
<220> FEATURE:
<223> OTHER INFORMATION: synthetic polynucleotide

<400> SEQUENCE: 6 aggaacccctt accgagctc                                              19